(12) United States Patent
Lee et al.

(10) Patent No.: US 7,968,856 B2
(45) Date of Patent: Jun. 28, 2011

(54) FLUOROMETER WITH LOW HEAT-GENERATING LIGHT SOURCE

(75) Inventors: Jerald D. Lee, Mendenhall, PA (US); Stanley D. Dabell, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/387,759

(22) Filed: May 6, 2009

(65) Prior Publication Data

US 2009/0230323 A1   Sep. 17, 2009

Related U.S. Application Data

(63) Continuation of application No. 12/052,212, filed on Mar. 20, 2008, now abandoned, which is a continuation of application No. 11/462,940, filed on Aug. 7, 2006, now abandoned, which is a continuation of application No. 10/863,535, filed on Jun. 8, 2004, now Pat. No. 7,109,495, which is a continuation of application No. 10/111,114, filed as application No. PCT/US00/30771 on Nov. 9, 2000, now Pat. No. 6,852,986.

(60) Provisional application No. 60/165,267, filed on Nov. 12, 1999.

(51) Int. Cl.
   *G01N 21/64* (2006.01)
(52) U.S. Cl. .................................................. 250/458.1
(58) Field of Classification Search ............... 250/458.1, 250/395, 459.1
   See application file for complete search history.

(56) References Cited

U.S. PATENT DOCUMENTS

| | | | |
|---|---|---|---|
| 3,919,545 A | 11/1975 | Schoon | |
| 4,683,202 A | 7/1987 | Mullis | |
| 5,038,852 A | 8/1991 | Johnson et al. | |
| 5,073,029 A | 12/1991 | Eberly et al. | |
| 5,243,540 A | 9/1993 | Van Albert et al. | |
| 5,315,375 A | 5/1994 | Allen | |
| 5,333,675 A | 8/1994 | Mullis et al. | |
| 5,436,718 A * | 7/1995 | Fernandes et al. | 356/73 |

(Continued)

FOREIGN PATENT DOCUMENTS

EP    0902271 A2    3/1999

(Continued)

OTHER PUBLICATIONS

Woolley et al., Functional Integration of PCR Amplification and Capillary . . . , Analytical Chemistry, 68:23, pp. 4081-4086, 1996.

(Continued)

*Primary Examiner* — David P Porta
*Assistant Examiner* — David S Baker
(74) *Attorney, Agent, or Firm* — Potter Anderson & Corroon LLP; Travis W. Bliss

(57) ABSTRACT

This invention concerns a fluorometer preferably combined with a thermal cycler useful in biochemical protocols such as polymerase chain reaction (PCR) and DNA melting curve analysis. The present fluorometer features a low heat-generating light source such as a light emitting diode (LED), having a one-to-one correspondence to each of a plurality of sample containers, such as capped PCR tubes in a standard titer tray. The fluorometer of the present invention further comprises an optical path between each LED and its correspondingly positioned container, and another optical path between each fluorescing sample within the positioned container and an optical signal sensing means. The instrument can be computer controlled.

20 Claims, 17 Drawing Sheets

U.S. PATENT DOCUMENTS

| | | | |
|---|---|---|---|
| 5,475,610 A | 12/1995 | Atwood et al. | |
| 5,543,018 A | 8/1996 | Stevens et al. | |
| 5,602,756 A | 2/1997 | Atwood et al. | |
| 5,736,333 A | 4/1998 | Livak et al. | |
| 5,854,684 A | 12/1998 | Stabile et al. | |
| 5,925,884 A | 7/1999 | Robinson et al. | |
| 6,005,663 A | 12/1999 | Waterhouse et al. | |
| 6,043,880 A * | 3/2000 | Andrews et al. | 356/311 |
| 6,046,859 A | 4/2000 | Raj | |
| 6,106,777 A | 8/2000 | Fujita et al. | |
| 6,132,996 A | 10/2000 | Hunicke-Smith | |
| 6,179,465 B1 | 1/2001 | Yam | |
| 6,255,118 B1 | 7/2001 | Alfano et al. | |
| 6,361,672 B1 | 3/2002 | Zhu et al. | |
| 6,444,461 B1 | 9/2002 | Knapp et al. | |
| 6,825,927 B2 | 11/2004 | Goldman et al. | |
| 6,852,986 B1 | 2/2005 | Lee et al. | |
| 7,109,495 B2 | 9/2006 | Lee et al. | |
| 2003/0016352 A1* | 1/2003 | Goldman et al. | 356/317 |
| 2003/0175813 A1 | 9/2003 | Pantoliano et al. | |
| 2006/0082768 A1 | 4/2006 | Wilson et al. | |
| 2007/0194246 A1 | 8/2007 | Lee et al. | |
| 2008/0212090 A1 | 9/2008 | Lee et al. | |

FOREIGN PATENT DOCUMENTS

| | | |
|---|---|---|
| EP | 0902271 A3 | 3/1999 |
| WO | WO 95/30139 A1 | 11/1995 |
| WO | WO 00/66777 A2 | 11/2000 |

OTHER PUBLICATIONS

Belgrader et al., Rapid Pathogen Detection Using a Microchip PCR Array Instrument, Clinical Chemistry, 44:10, pp. 2191-2194, 1998.

Northrup et al., A Miniature Analytical Instrument for Nucleic Acids Based on Micromachined Silicon . . . , Analytical Chemistry, 70:5, pp. 918-922, 1998.

Ibrahim et al., Real-Time Microchip PCR for Detecting Single-Base Differences in Viral and Human DNA, Analytical Chemistry, 70:9, pp. 2013-2017, 1998.

International Search Report in International Application No. PCT/US2000/030771, mailed Mar. 15, 2001.

Non-Final Office Action in U.S. Appl. No. 11/462,940, mailed Sep. 25, 2007.

Non-Final Office Action in U.S. Appl. No. 12/052,212, mailed Nov. 6, 2008. 11.

* cited by examiner

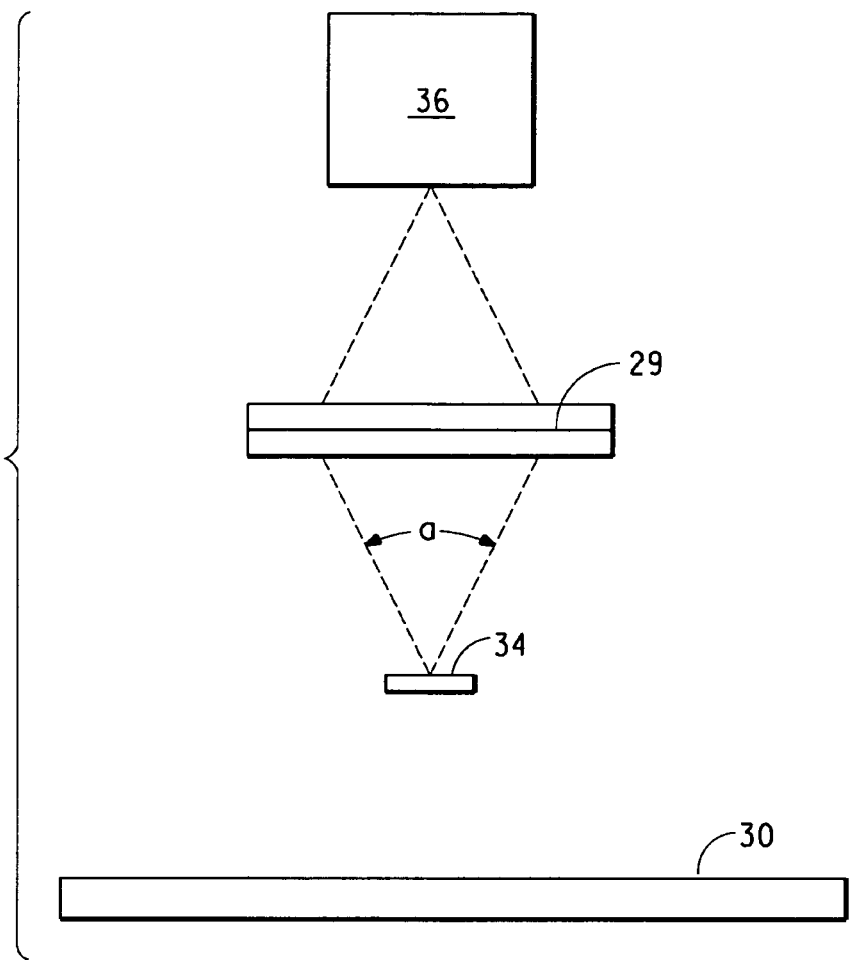
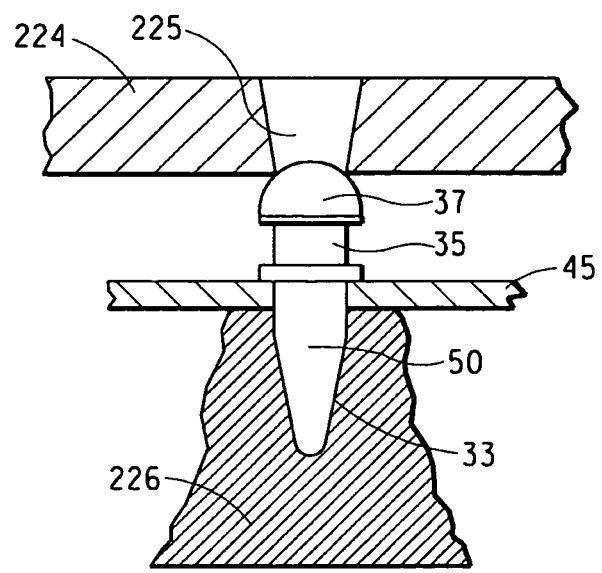

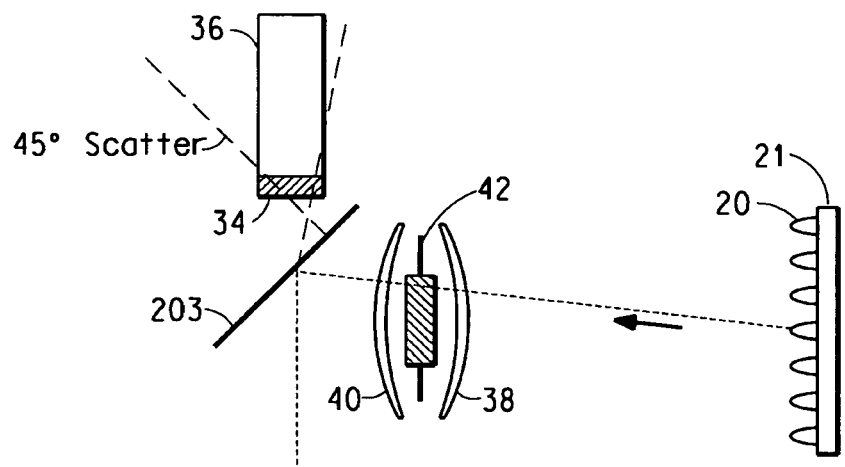
FIG. 13
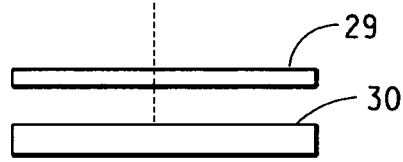
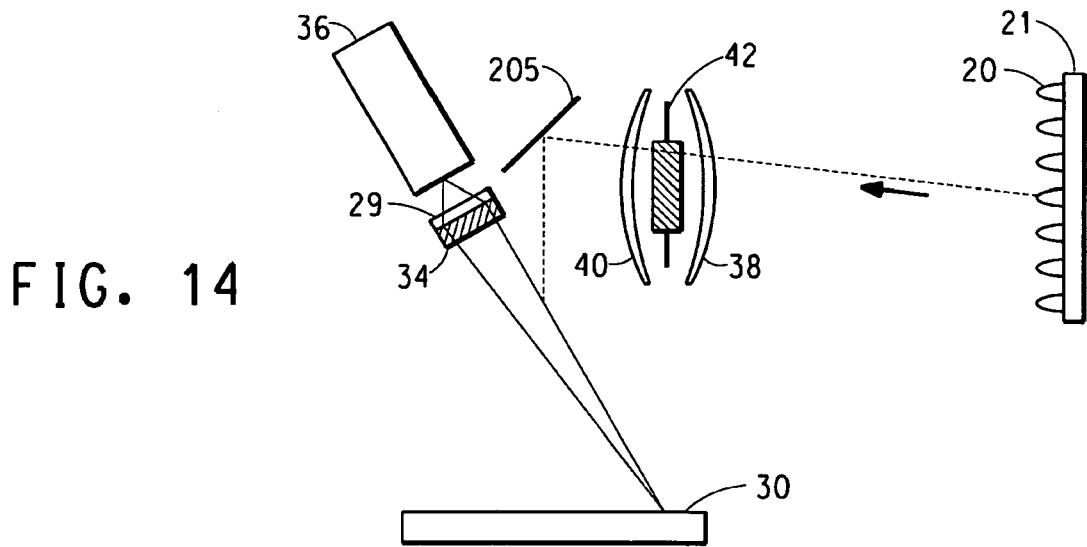
FIG. 14

FLUOROMETER WITH LOW HEAT-GENERATING LIGHT SOURCE

This application is a continuation of U.S. application Ser. No. 11/462,940, filed Aug. 7, 2006, which is a continuation of U.S. application Ser. No. 10/863,535 filed Jun. 8, 2004, now U.S. Pat. No. 7,109,495, which is a continuation of U.S. application Ser. No. 10/111,114, filed Apr. 19, 2002, now U.S. Pat. No. 6,852,986, which is a National Stage Application of PCT/US00/30771, filed Nov. 9, 2000, which claims the benefit of U.S. Provisional Application No. 60/165,267, filed Nov. 12, 1999.

FIELD OF THE INVENTION

This invention relates to instrumentation, particularly to instruments for detecting and measuring fluorescence, and more particularly to fluorescence measurements usable in conjunction with a variety of applications including use in assays based on polymerase chain reaction (PCR).

BACKGROUND OF THE INVENTION

Many reactions are characterized by the occurrence, or changes in level, of fluorescence when illuminated by a suitable excitation wavelength. In these types of reactions, a fluorescent sample absorbs light of a given wavelength and, in response thereto, emits light of a different wavelength.

Fluorescence may be inherent in the involved reagents or it may be provided deliberately by a suitable marker incorporated in the reactants. Hence, instruments for measuring fluorescence, fluorometers, are commonplace in the laboratory environment.

Several difficulties exist with many stand-alone fluorometers and those combined with other instrumentation. First, it is difficult to obtain very high intensity light in the proper wavelength from instruments which utilize a halogen or laser unitary light source without generating a large amount of heat. Similarly, since tungsten lights and the like must be on continuously to reach and operate under stable conditions, they also generate a large amount of heat. This large amount of heat can shorten the life of the lamp and should be dissipated because it may heat up the sample, thereby changing its fluorescent light emitting characteristics. Thus, these types of instruments require extensive cooling for the light source, and such light sources require frequent replacement.

In addition, for those instruments in which a group of samples may be tested simultaneously, a great deal of excitation light energy can be lost through diversion between the samples. This translates into a lower excitation efficiency.

Other fluorometers either lack sufficient sensitivity or are so expensive in construction as to be impractical for many purposes. For example, many fluorometers with a halogen light source do not have adequate sensitivity. This type of fluorometer has a limited dynamic range since all samples are illuminated and imaged at the same time if a typical charge coupled device (CCD) type camera is used. A laser light source type fluorometer can have better performance, but the laser light source is more expensive.

Many protocols, particularly in the broad field of microbiology, require repetitive, controlled temperature regimes. Apparatus filling this need are called "thermal cyclers". It is useful to combine fluorometers with thermal cyclers for facilitating receipt of results which depend on fluorescence measurements to indicate reactions. One protocol which utilizes a thermal cycler is the polymerase chain reaction (PCR) (see U.S. Pat. No. 4,683,202 (Mullis)). To determine if amplification has occurred at the end of PCR, fluorescent dyes may be used as indicators, particularly intercalating dyes that fluoresce when bound to double stranded DNA but do not bind, or bind very inefficiently to single strands and have no or little signal in the presence of single strands.

Certain commercially available fluorometer/thermal cyclers can accommodate a standard ninety-six well tray of reaction tubes and include a fluorometer which uses a single, powerful incandescent light source to project light through an optical system to illuminate the tray and excite the fluorescent dyes therein to indicate positive reactions. Other commercially available instruments use a laser instead of an incandescent light source and a mechanical scanning device to isolate the signal from a reaction tube via a fiber optic cable onto a photodiode array.

FIG. 1 depicts a schematic of a system similar to certain commercially available instruments. It uses a single incandescent light source, lamp 1, which is a halogen projection lamp. Cooling is provided by a fan not shown. The light output passes through shutter 2 which is actuated by means not shown to shield the system when measurements are not being made. The light is directed toward the entirety of the sample tubes, not shown, held in sample plate 10 which is in intimate contact with a heating/cooling block 3 and in coordination with a data accumulation system not shown. Standard plates, or "trays", used in this system hold 96 tubes. The directed beam of light passes through an excitation filter 4. The filtered light from filter 4 passes rectangular aperture 5 to confine the light to the sample tray area. Beamsplitter 6 reflects the light toward beam folding mirror 7. The light is then directed to fresnel lens 8. Fresnel lens 8 directs the light onto individual lenses mounted in plate 9, one lens per sample tube carried by plate 10. Once the light contacts the sample material any emitted light passes through beam splitter 6 and then through emission filter 11, lens 12, and into CCD type camera 13. CCD type camera 13 acquires an image of the entire sample tray. A computer program is used to calculate the fluorescent intensity of each sample tube from the image. The power measured by CCD type camera 13 indicates the reaction in the individual tube.

Other commercially available systems use an argon ion laser as the light source. In these systems, light from the argon ion laser passes through a dichroic mirror, a lens and a multiplexer which provides a fiber optic cable for each well of a 96-well plate. Excited light returns to the mirror and is reflected into a spectrograph which separates the light into a pattern that falls on a linear CCD detector. Appropriate filters are included in the optical paths.

Another commercially available system is partially depicted schematically in FIG. 1a. This instrument combines a "microvolume fluorometer" with thermal cycler 120. The light source in this instrument is a single light emitting diode (LED) 100 which projects light through lens and filter 102 to dichroic mirror 103 to reading lens 104 and then to the bottom of reaction tube 106. The reaction tubes, thirty-six in number, are held in carousel 108 which is stepped by motor 110 to place each tube in sequence over the reading lens 104. Any resultant emission reflects from mirror 103 and from one of the dichroic, color selective mirrors 114 through lenses 116 to one of photohybrids 118. A signal then is processed in an associated computer and printer not shown. The cycler 120 is air-cooled and heated using fan motor and associated fan blades 112 and heater coil 122 driving heated or cold air as directed by the program within the computer. Motor 124 positions the optical system as required. This system is not suited to a standard 8 by 12 tray and is expensive because it requires complex positioning mechanisms to present the tubes to the fluorometry system.

In view of the problems discussed above, there is a need to provide an inexpensive fluorometer having either a simple positioning mechanism or no positioning mechanism. In addition, there is a need for a fluorometer characterized by low heat-generating light sources using minimal power and which eliminates waste of excitation energy. There is also a need to provide light sources with rapid stabilization. Further, there exists a need for a highly sensitive fluorometer with an improved signal to noise ratio.

SUMMARY OF THE INVENTION

The present invention concerns a fluorometer, comprising: plurality of low heat-generating light sources; means for positioning a plurality of containers for containing potentially fluorescing sample into optical communication with said light sources, wherein each light source corresponds with one of said containers when said container is in position; a first optical path means for directing light from said light source to said corresponding container; optionally an excitation filter in said first optical path means for allowing transmission therethrough of an excitation wavelength from the light generated from each light source; an optical signal sensing means in optical communication with any fluorescing sample in said positioned containers; a second optical path means for directing emitted light from any fluorescing sample to said optical signal sensing means; and optionally an emission filter in said second optical path for allowing transmission therethrough of emitted light from any fluorescing sample and for substantially blocking transmission of light of wavelengths other than the wavelengths of said emitted light.

The present invention also concerns a combined fluorometer and thermal cycler, comprising the fluorometer described above, wherein the containers are sample tubes, in combination with a thermal cycler, said thermal cycler comprising: a thermally controlled base having a plurality of wells, each well capable of holding a capped sample tube, or the tube portions of an integral tube/holder, in close contact; a thermally controlled cover having a plurality of apertures corresponding to each sample tube, said cover in operative condition mechanically biasing the cap of each said sample tube into said close contact, each said aperture expanding outward from said cap; and programmable control means for controlling the temperature of said sample tubes according to a selected protocol.

The present invention further concerns a method for detecting a fluorescence signal from polymerase chain reaction amplified material, comprising the steps of: positioning the material into optical communication with the light sources of the fluorometer of the present invention described above; exposing the material to an excitation wavelength; detecting the emitted light with the optical signal sensing means; and comparing a differential of the emitted light level to a predetermined reference level.

BRIEF DESCRIPTION OF THE DRAWINGS

FIG. 11 is a schematic view of an optical arrangement for the second optical path means of the present invention.

FIG. 12 shows an embodiment of the heating cover shown in FIG. 8 of the present invention.

FIG. 13 is a schematic diagram showing elements of the present invention including a dichroic mirror.

FIG. 14 is a schematic diagram of another embodiment of the present invention.

FIG. 18b is the electrical schematic for the component layout of FIG. 18a.

DETAILED DESCRIPTION OF THE INVENTION

To circumvent the difficulties described above, the fluorometer of the present invention preferably uses a plurality of light emitting diodes (LEDs) as the light sources. By using LEDs, a large amount of heat is not generated, thereby minimizing sample heating, easing heat dissipation problems, and extending the life of the light source. In addition, by providing a one-to-one correspondence of light source to sample container with the directed light falling inside the container, waste of excitation energy is largely eliminated allowing for the use of a light source that uses minimal power.

In addition to the advantageous arrangement of components of the first and second optical paths means, the present invention also has the benefit that for the plurality of potentially fluorescing samples, there is an equal number of low heat-generating light sources, and the output of any one of the light sources is dedicated to a particular, correspondingly positioned container containing the potentially fluorescing samples in an optical system in which the positioning means, such as a sample tube tray, can be viewed by an optical signal sensing means.

The present invention concerns a fluorometer, comprising a plurality of low heat-generating light sources; means for positioning a plurality of containers for containing potentially fluorescing sample into optical communication with the plurality of light sources, wherein each light source corresponds with one of said containers when said container is in position; a first optical path means for guiding light from said light source to said corresponding container; an excitation filter in said first optical path means for allowing transmission therethrough of an excitation wavelength from light generated from each light source; an optical signal sensing means in optical communication with any fluorescing sample in said positioned containers; a second optical path means for directing emitted light from any fluorescing sample to said optical signal sensing means; and an emission filter in said second optical path for allowing transmission therethrough of emitted light from any fluorescing sample and for substantially blocking transmission of light of wavelengths other than the wavelengths of said emitted light.

Figure 2:
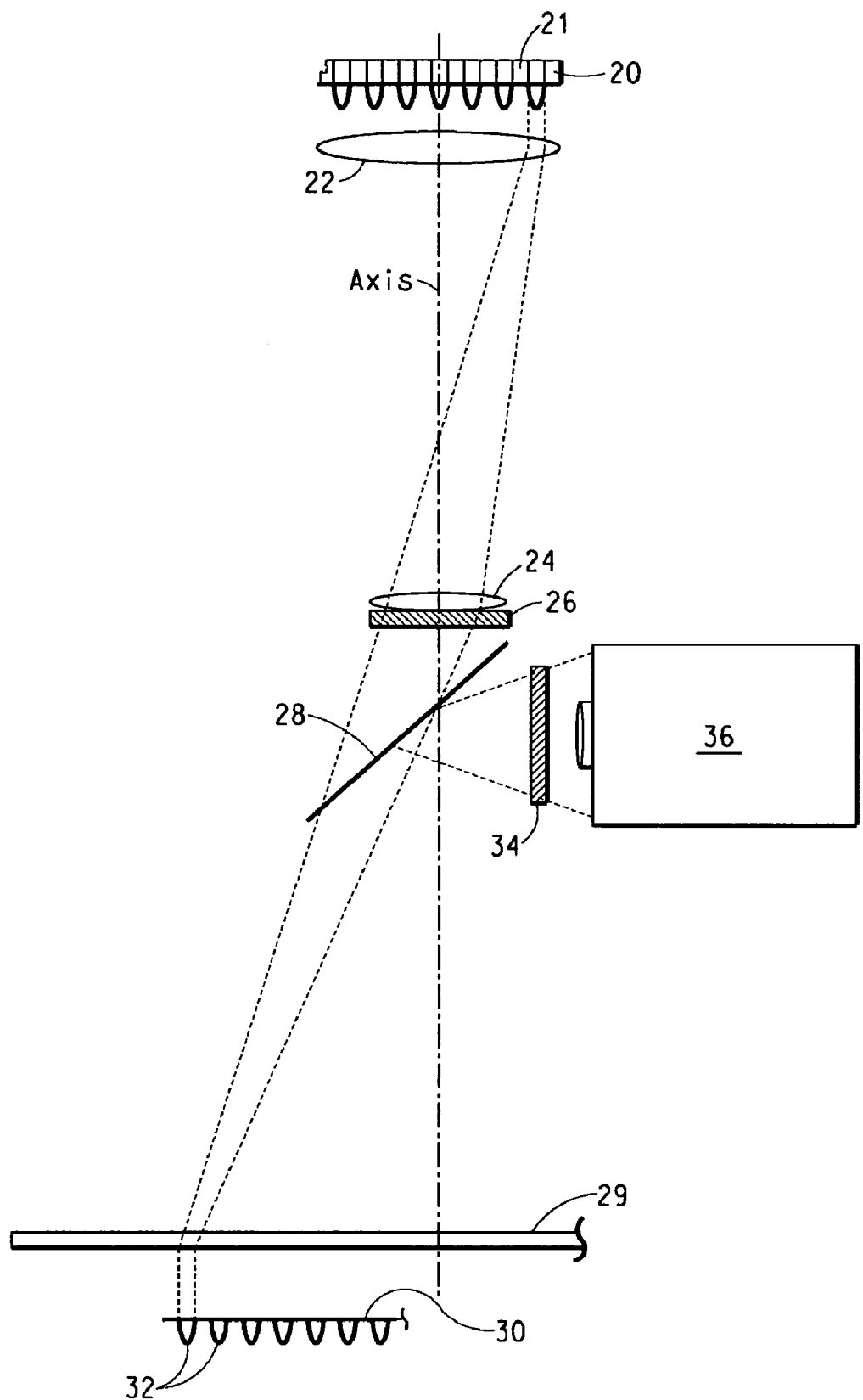
FIG. 2 is a schematic drawing of one embodiment of the present invention.

As shown in FIG. 2, the fluorometer of the present invention includes a plurality of low heat-generating light sources 20. By "low heat-generating" is meant below the level at which active cooling of the light source, such as via a fan, is required. Such low heat-generating light sources generally use only low or minimal power for energizing. The light sources used are capable of emitting a wavelength that can excite an indicator in a sample. Each light source is in optical communication with the potentially fluorescing sample when the container containing such sample and with which such light source corresponds, is placed in position in the fluorometer where such optical communication can occur. Suitable light sources for use in the present invention are solid state light sources including laser diodes and light emitting diodes. A preferred light source is a light emitting diode (LED). In a preferred embodiment of the present invention, the LEDs are blue LEDs. NSPB500S LEDs are available from Nichia Corp. (3775 Hempland Road, Mountville, Pa. 17554) and are suitable LEDs for the present invention. Blue LEDs are preferred because the preferred intercalating dye, SYBR Green (available from Molecular Probes, Inc., 4849 Pitchford Ave. Eugene, Oreg. 97402), is sensitive to the exciting wavelength of blue. If other fluorescing materials are used in the sample material, it is a simple matter to switch to an alternative LED light source color and excitation filter that will excite a given dye.

The low heat-generating light sources of the present invention can provide adequate power to the potentially fluorescing sample contained in the light sources' corresponding positioned containers because in the present invention light is not wasted on the spaces in between the positioned containers. One low heat-generating light source is provided for each of the containers in a one-to-one correspondence. There is an array of low heat-generating light sources. A representative example of the array of low heat-generating light sources 20 can be seen in FIG. 2.

Figure 7:
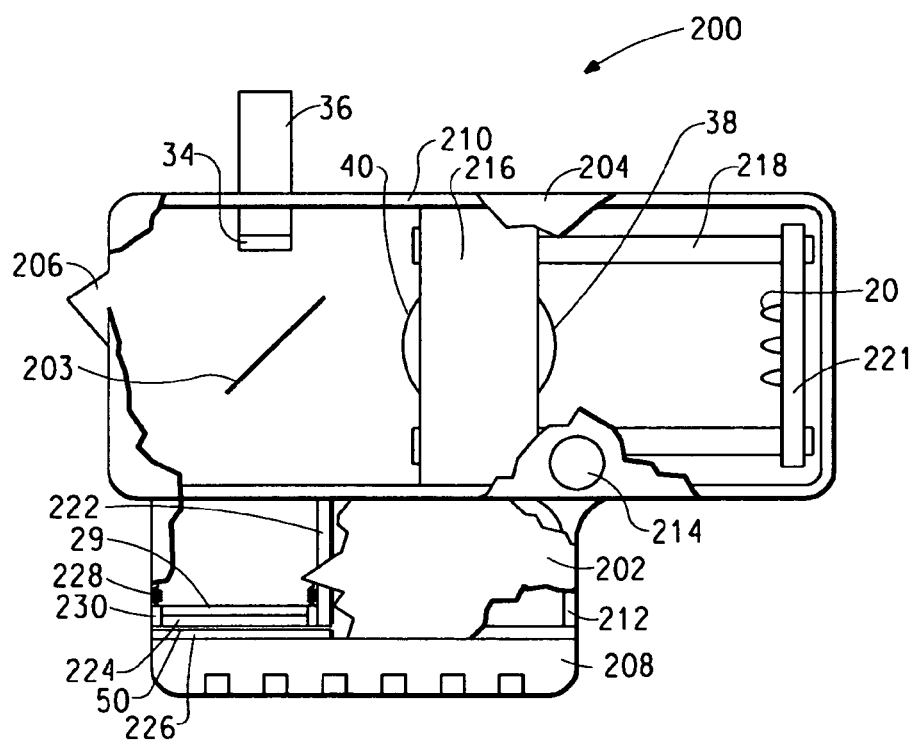
FIG. 7 is a schematic view of elements of the combined thermal cycler and fluorometer of FIG. 6 as seen by partially breaking away the near side of the covers thereof.
Figure 20:
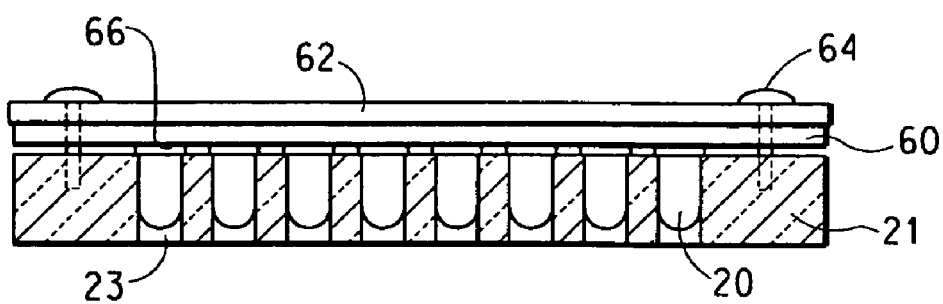
FIG. 20 is an elevational, sectional view of one embodiment for mounting the light sources of the present invention.

As shown in FIGS. 2, 3, 4, 5, 10, 13, 14, 15a, 15b, and 20, light source holder 21 can be used for mounting or carrying light sources 20. As shown in FIG. 7 for a combined fluorometer and thermal cycler of the present invention described in more detail below, a light source support plate 221 can be used to carry the light sources 20, such as an array of LEDs. The light sources can be held or mounted in such holders or support plates in drilled cavities and can be held with cement or other suitable adhesive after careful aiming toward a particular optic in the first optical path means, shown for example in FIG. 7 as the center of lens 38. In FIG. 20 another embodiment for a means for mounting the light sources is shown. Light sources 20, preferably LEDs, can be press fit into holes 23 in light source holder 21. This places the inner part of flanges 66, which are smooth and fairly perpendicular to the axis of light sources 20 against the surface of light source holder 21. A sheet of soft rubber or other elastomer 60 covers the other side of light sources 20 and is perforated so that two electrical leads, not shown, on each light source 20 can pass through and enter holes in circuit board 62. This assembly can be held under pressure by fasteners 64. To prepare this assembly, sheet 60 is placed on top of circuit board 62, which may be part of a computer, such as a PC. The leads of light sources 20 are inserted into circuit board 62 through sheet 60 and circuit board 62 is placed over light source holder 21 so that each light source 20 is in its hole 23. Fasteners 64 are inserted and torqued. The leads can then be soldered to circuit board 62. This embodiment firmly mounts light sources 20. Proper mounting of light source holder 21 assures aiming of light sources 20.

The mounting for the low heat-generating light sources can be adjusted to provide any reasonable ratio of spacing between each light source desired to suit design considerations. Preferably, a symmetrical spacing arrangement for both the low heat-generating light sources and their corresponding containers is used. The distances between each light source can be equal. This equal distance, however, is only a matter of convenience and suits the commercially available 96 sample tube holders that can be used as positioning means in the present fluorometer.

Figure 9A:
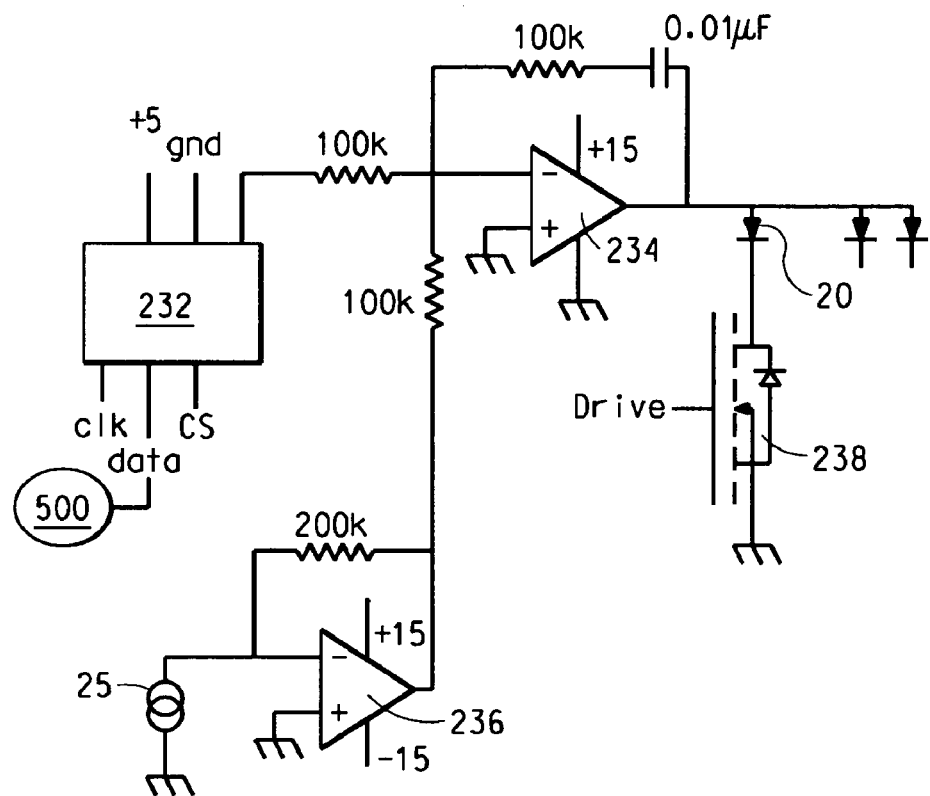
FIG. 9a is an electrical schematic showing feedback control of a light source.
Figure 9B:
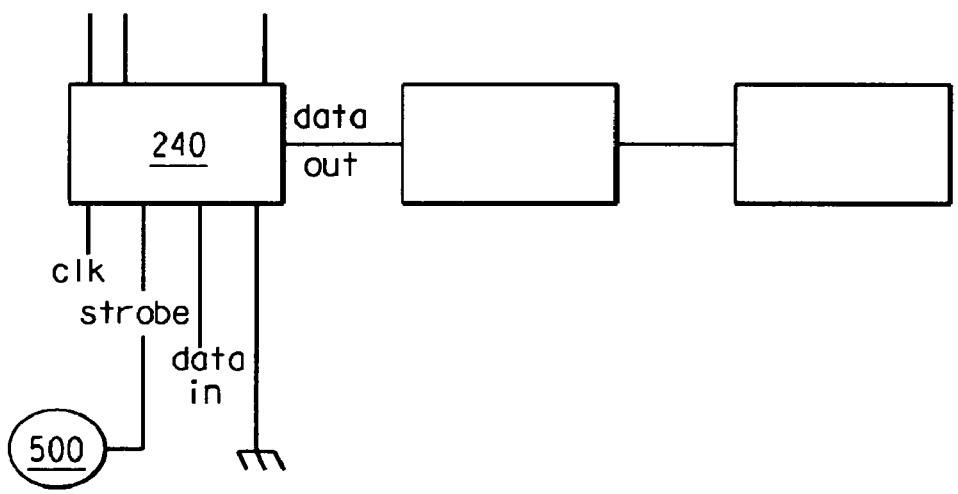
FIG. 9b is an electrical block diagram of the LED selection circuitry.
Figure 9C:
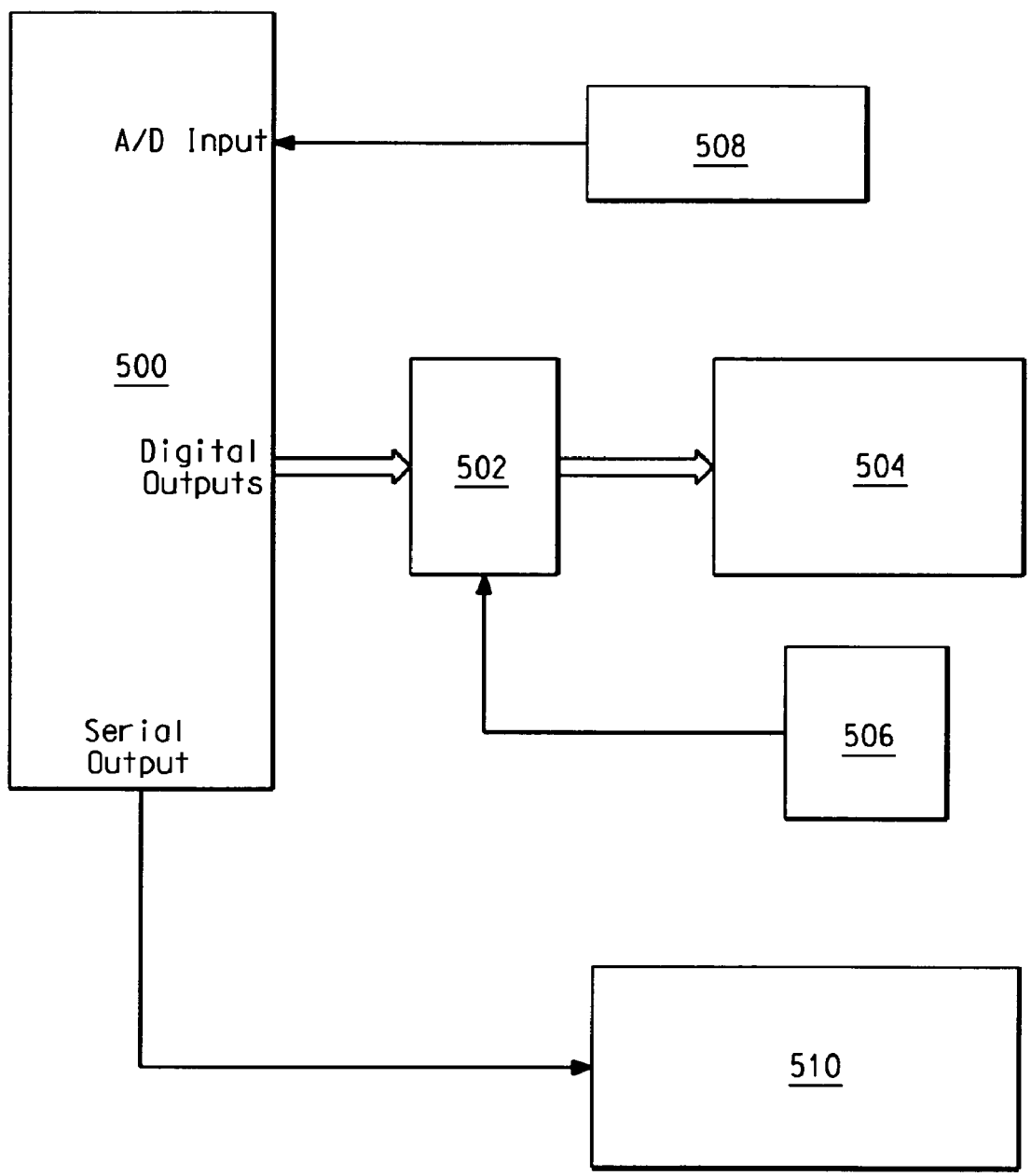
FIG. 9c is an electrical block diagram of one embodiment for the programmable control means for the present invention.

The present fluorometer can further comprise means for powering each of the low heat-generating light sources (see, for example, FIG. 9c). Each light source can be energized simply by attaching it to a power source. Alternatively, each light source can be powered in a selected sequence by programmable control means, such as a computer. Powering means can be capable of powering each light source sequentially, simultaneously, randomly, or any combination thereof. If there are a fewer number of containers than the number of light sources, this can be easily accommodated through programmable control means, whereby either the light source corresponding to a position within the positioning means without a container may not be powered and/or have its optical signal sensed. Another method of driving an array of LEDs is to use a crosspoint switch arrangement. The anodes of each column of LEDs are wired in parallel. The cathodes of each row of LEDs are also wired in parallel, A single LED is illuminated by selecting the desired row and column. Column signals may be switched by PNP transistors connected to a positive supply voltage. Row signals may be switched by NPN transistors connected to ground.

FIG. 9b shows three thirty-two channel serial-to-parallel converters 240 that can form half of the electrical drive circuitry that can be used to power the LEDs of one embodiment of the present invention. HV51s with open drain outputs available from Supertex, Inc. (1235 Bordeaux Drive, Sunnyvale, Calif. 94089) can be used as such converters. One of these channels is shown in FIG. 9a as 238 which shows the other half of the LED drive circuitry. In the circuitry shown, digital-to-analog (D/A) converter 232, such as a LTC 1446 by Linear Technology Corporation (15 Research Place, North Chelmsford, Mass. 01863), provides an output of 0 to 5 volts. Summing amplifier 234, such as an LM2904 by National Semiconductor Corporation (2900 Semiconductor Drive, Santa Clara, Calif. 95051), compares the D/A output to that of the output of trans-impedance amplifier 236, such as a CA3140 by Intersil, Corp. (2401 Palm Bay Road, N.E., Palm Bay, Fla. 32905), which is driven by optional detector 25, such as a silicon photodiode VTD34 available from PerkinElmer Analytical Instruments (761 Main Avenue, Norwalk, Conn. 06859). Summing amplifier 234 causes these two voltages to be equal in magnitude. Detector 25 and trans-impedance amplifier 236 should be arranged to insure that the output voltages from D/A converter 232 and trans-impedance amplifier 236 are opposite in sign. In this embodiment, the light intensity of an LED light source is pinned to a reference voltage. This reference voltage can be set by programmable control means 500, such as a computer, via D/A converter 232 to uniformize the output of the plurality of light sources.

As mentioned above, the present fluorometer may further comprise means for uniformizing the output from the low heat-generating light sources. By "uniformizing the output" is meant that the intensity of each light source is measured and adjusted, if necessary, to ensure that the intensity of light from each light source is equal to that of the other light sources in the fluorometer. A variation in the light beam intensity sensed by the uniformizing means is used to correspondingly increase or decrease the voltage of the power source for the light source so as to maintain the light beam intensity constant and at a predetermined level. Consequently, variations in the light beam intensity due to fluctuations in the power supply voltage, the age of the light source and the like are prevented from affecting the fluorescent emissions by the particles in the sample being tested.

Figure 3:
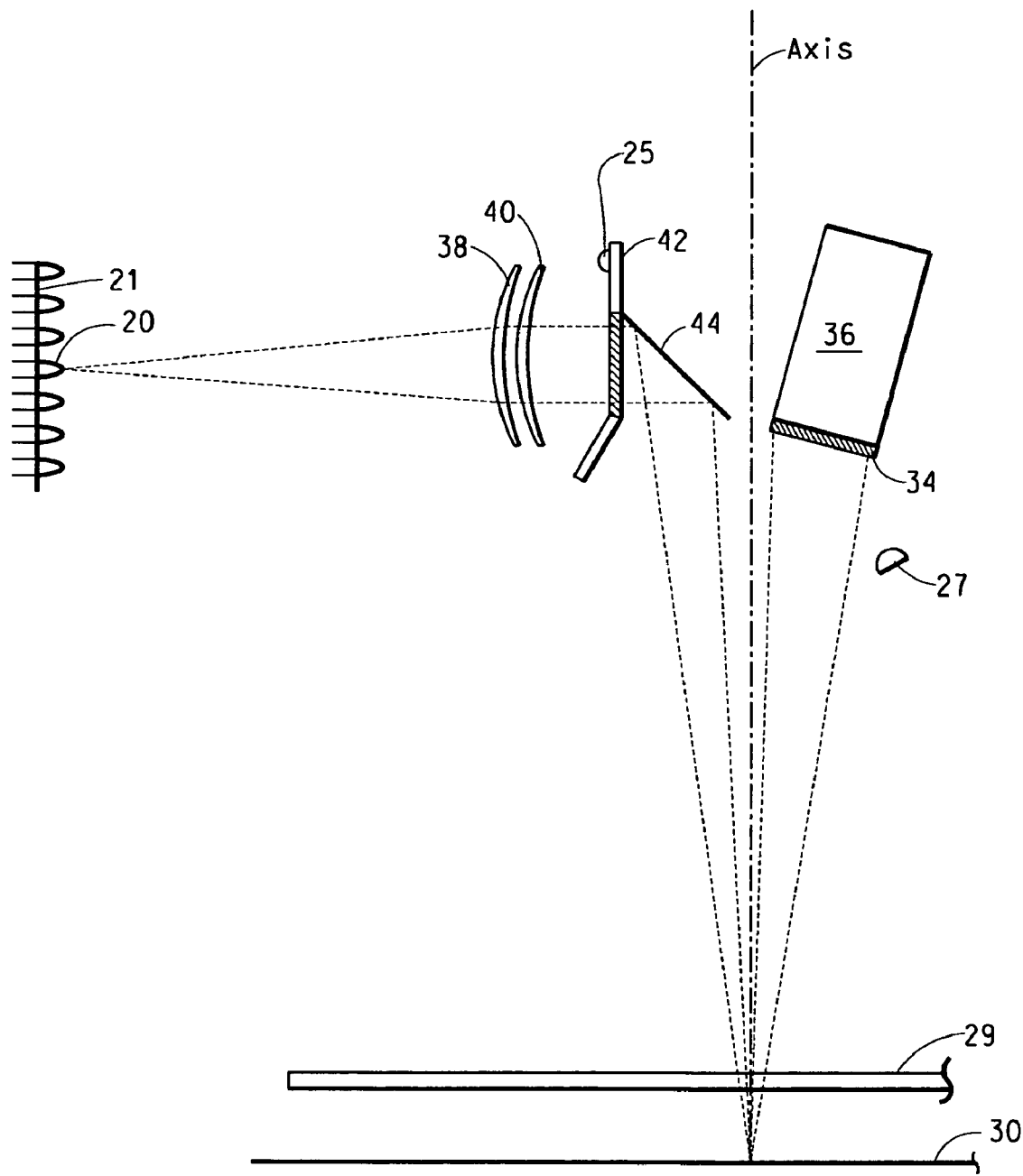
FIG. 3 is a schematic drawing of an off-axis embodiment of the present invention.

One embodiment of a uniformizing means is shown in FIG. 3 as detector 25 and one embodiment for associated circuitry is shown in FIGS. 9a and 9b, as was discussed above. A preferred uniformizing means is a silicon photodiode and its associated feed-back circuitry. The uniformizing means is preferably located in a position where the light from each of the low heat-generating light sources can fall upon it. For example, in FIG. 3, such a location is adjacent to excitation filter 42 between meniscus lenses 38, 40, or on the far side of excitation filter 42 from light sources 20. Another suitable location can be in the center of excitation filter 42, as shown. A relatively small uniformizing means is preferred so the light going toward the positioned containers is not excessively blocked.

Quantitatively, the fluorescent emissions of the excited sample in the container are a function of the intensity of the excitation light beam from light source and the concentration of fluorescent particles in the sample, or the total number of fluorescent particles in the sample cell. Thus, any fluctuation in the intensity of the excitation light beam would result in a corresponding change in the intensity of the fluorescent emissions and cause an error which is a function of the intensity change in the excitation beam.

Figure 18A:
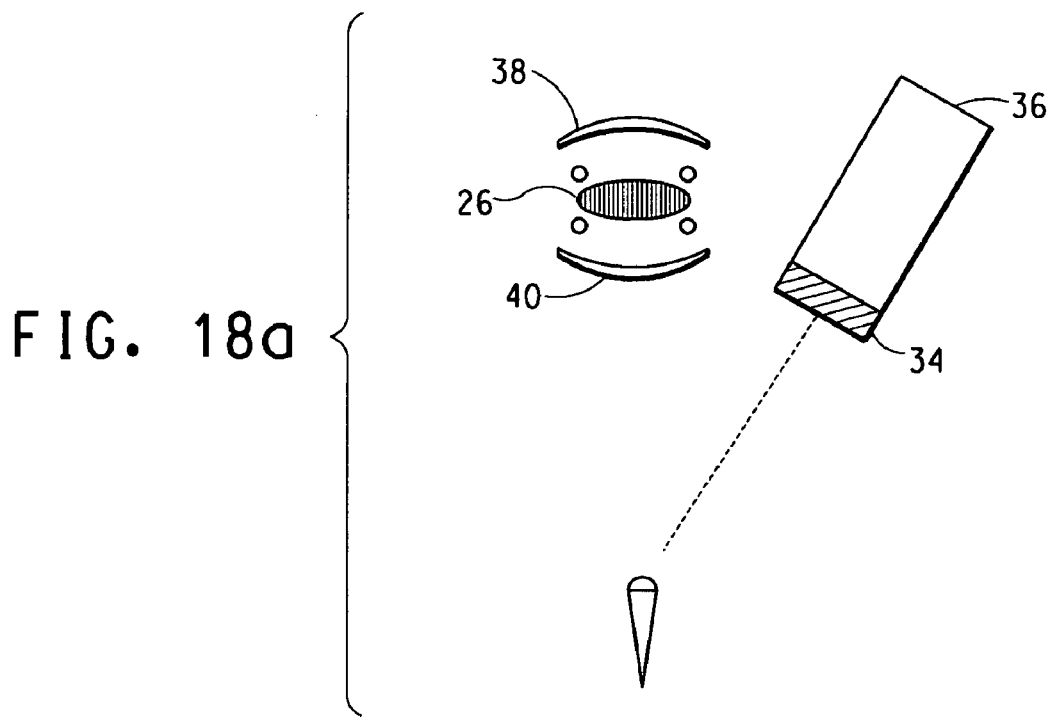
FIG. 18a and 18b are schematics showing one embodiment for compensating for changes in light source output where
Figure 18B:
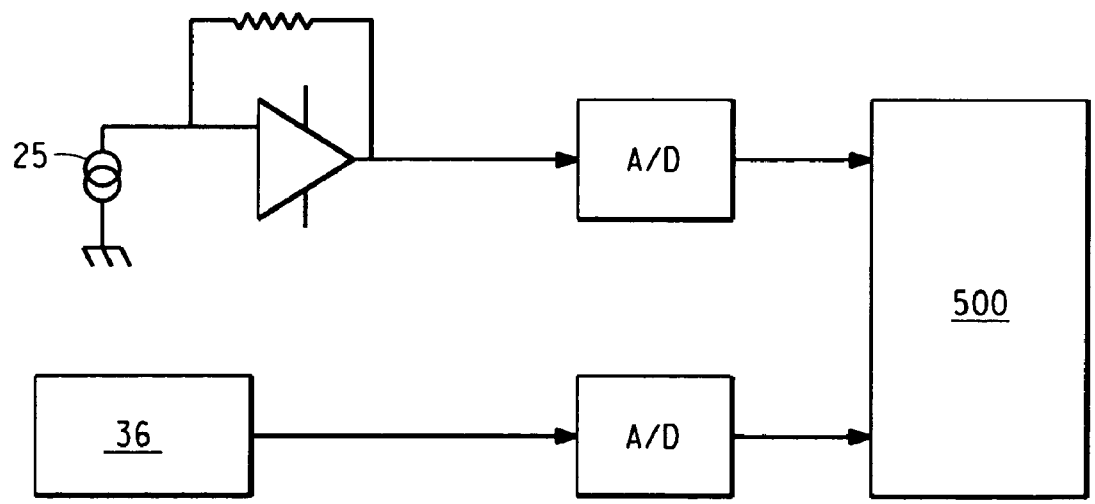

Because the LEDs 20 are operated at a nominally high current, there is not much room for a further increase in current should the feedback circuit described previously call for more. Another approach, therefore, indicated schematically in FIG. 18a and appropriate circuitry in FIG. 18b, is to supply the LEDs with an unvarying current and to form a ratio between the sample signal measured by optical signal sensing means 36 and the signal produced by at least one silicon photodiode 25 monitoring the LED output. In this way variations in sample signal are compensated as the LED output changes.

Another technique for uniformizing the output of the light sources is to allow the array of LEDs to excite a calibration phosphor. The calibration phosphor can be a sheet of plastic that fluoresces, such as the ULTEM® type polyetherimide, available from AIN Plastics, Inc. (249 E. Sandford Blvd, Mount Vernon, N.Y. 10550), which can withstand temperatures as high as 200° C. The intensity of light emitted for each source is recorded and normalized using the detected signals from the phosphor.

The fluorometer of the present invention includes means for positioning a plurality of containers for containing potentially fluorescing sample into optical communication with said light sources, wherein each light source corresponds with one of said containers when in position. Such positioning means include a sample plate, a titer plate, a sample holder, a sample tray, a carriage, or other transport device known by those of skill in the art as capable of holding or accommodating a plurality of containers for containing potentially fluorescing samples.

The positioning means containing the containers is mounted or positioned in the fluorometer in such a manner as to place the containers (and likewise the potentially fluorescing samples) into optical communication with the corresponding light source.

The containers can include containers capable of being separated from the positioning means or can be integrally formed within the positioning means. Alternatively, the containers can be wells formed within the positioning means that are capable of holding the potentially fluorescing sample. Each embodiment will be of a size that will fit the particular configuration of the fluorometer. Preferably, the containers are sample tubes. Sample tubes suitable for the present invention are commercially available. Containers 32 are shown in FIG. 2 as being held in positioning means which is shown as sample plate 30 which can be a titer plate. Preferably, there is an array of containers held by the positioning means. Most preferably, the positioning means and containers together are an array of 8 sample tubes by 12 sample tubes to total 96 held in a sample plate. The containers can be capped or covered by other means known in the art. As used herein "cap" includes caps and other covers for sealing containers.

The present fluorometer includes a first optical path means for directing light from said plurality of low heat-generating light sources to a potentially fluorescing sample in the corresponding positioned container. Thus, said first optical path means optically connects each low heat-generating light source to its corresponding positioned container via one of a variety of optical arrangements. The first optical path means can include a variety of optics of conventional construction. The particular arrangement of the optical components along the first optical path can be adjusted to provide any reasonable ratio of spacing desired to suit design considerations. Suitable optics for guiding light can include at least one of the following: a lens, including a condensing lens, an objective lens, a fresnel lens, an imaging lens, a positive lens, or a field lens, a reflector, such as a mirror, a beam splitter, and an excitation filter. These optics and other useful optics are well known in the art and are commercially available. Methods of mounting such optics are also well known in the art. FIGS. 2, 3, 4, 5, 7, 13, 14, 15a, 15b and 16 show different embodiments for arrangements of a variety of optics of the first optical path means. The first optical path means can include optics to guide light in a straight path, a relatively straight path, as shown in FIG. 2, angled, or the first optical path can be folded, for example, by using at least one reflector 44 as is shown in FIG. 3.

In FIG. 2, light is shown as emitted from light source 20, which light is guided along first optical path means which includes first field lens 22, imaging lens 24 positioned proximate excitation filter 26, dichroic reflector 28, second field lens 29, which can be a fresnel type lens, and falls on a single corresponding positioned container 32. The first optical path is traced in FIG. 2 with dashed lines from light sources 20, shown here as held in light source holder 21, to their corresponding containers 32.

FIG. 3 shows an "off-axis" variant of the arrangement of first and second optical path means of the present fluorometer. This embodiment provides a configuration which eliminates the splitter beam and avoids the large wavelength shift of a 45 degree dichroic reflector. In the embodiment shown in FIG. 3, light from the energized light sources 20 passes through two meniscus lenses 38 and 40, and then passes to excitation filter and stop 42. The stop is an opaque area surrounding the excitation filter. The embodiment shown in FIG. 3 further comprises mirror 44, shown here as a front surface mirror, which acts to bend the axis of the light that passed through excitation filter 42 to about 45 degrees whereupon it travels to field lens 29. Field lens 29 then directs the light onto the sample in positioned container, not shown, held in sample plate 30.

Figure 4:
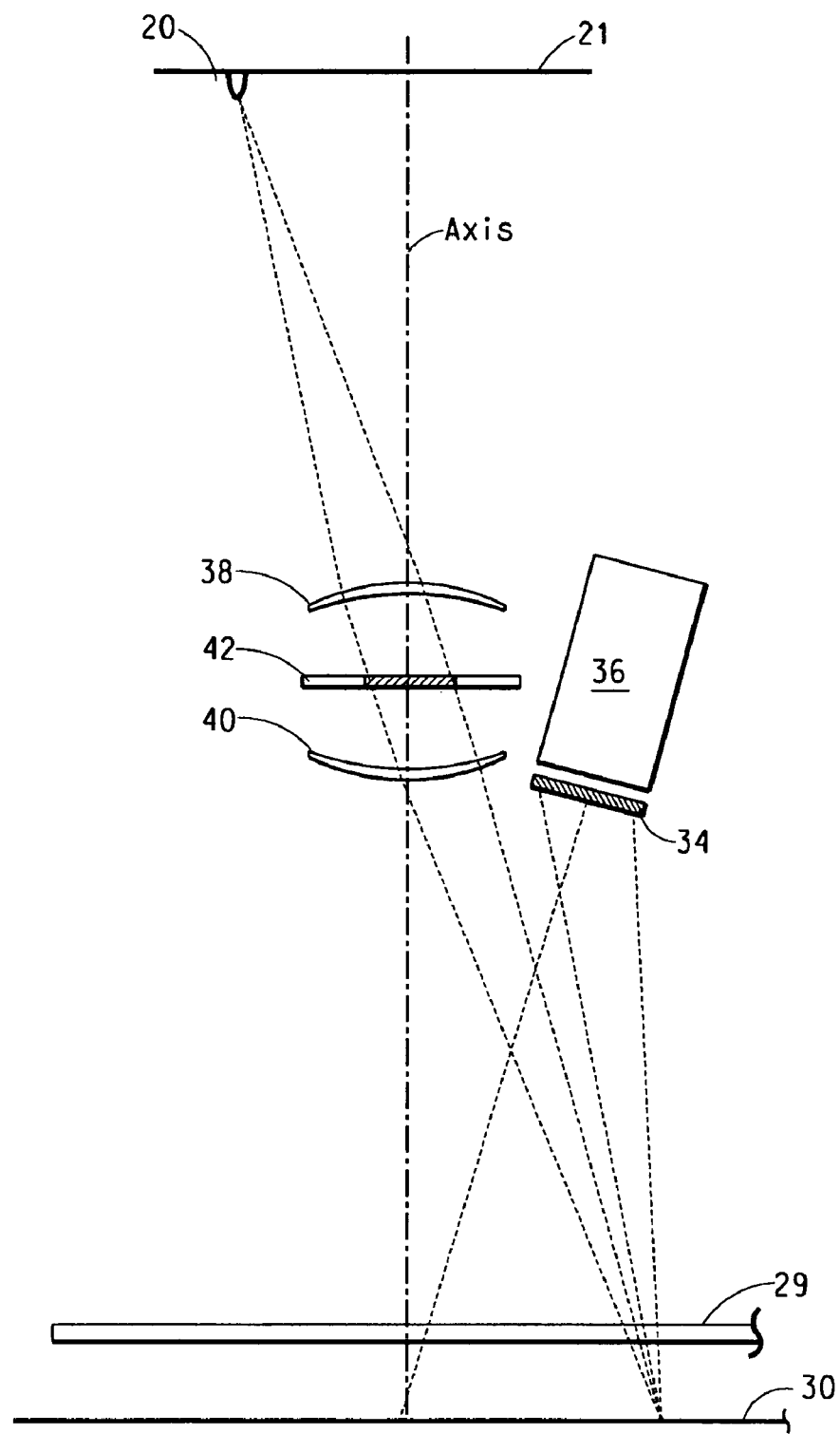
FIG. 4 is a schematic drawing an off-axis of another embodiment of the present invention.

FIG. 4 illustrates another off-axis embodiment of the present invention. In this embodiment, light travels from each light source 20 held in light source holder 21 and passes through a pair of meniscus lenses 38 and 40. In this preferred embodiment, one such meniscus lens is disposed on either side of excitation filter 42. The light travels further along the first optical path means to field lens 29, which can be a fresnel lens.

Figure 5:
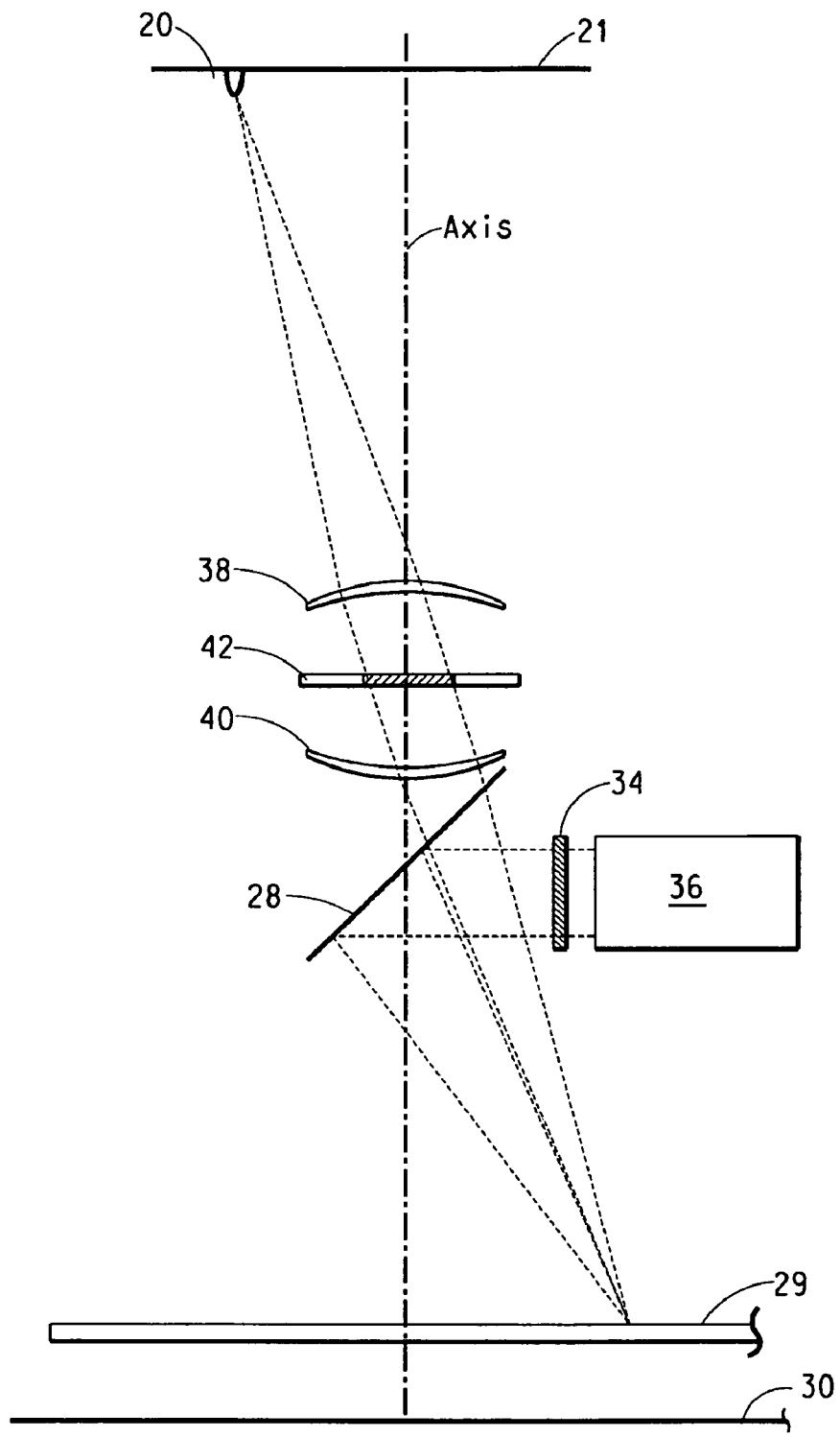
FIG. 5 is a schematic drawing of yet another embodiment of the present invention.

Referring now to FIG. 5, a variant of the arrangement of components of FIG. 2 is shown employing different optics. In this arrangement, lenses 22 and 24 (of FIG. 2) are replaced by meniscus lenses 38 and 40 as in FIG. 3, and filter 26 is replaced by a excitation filter and stop 42. Beam splitter 28 is used.

Figure 8:
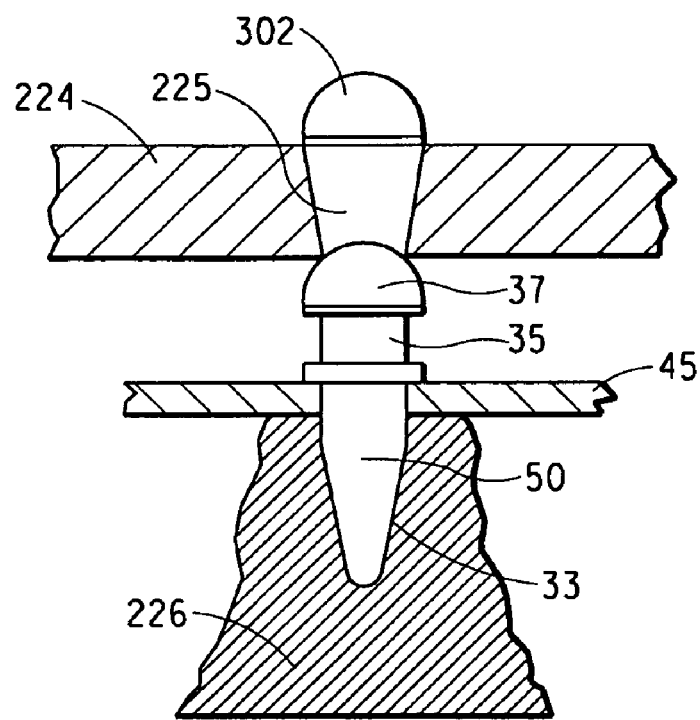
FIG. 8 is a cross-sectional view of a sample tube held in a temperature controlled well with a heating cover.
Figure 10:
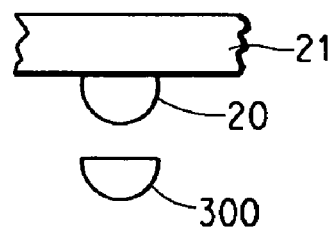
FIG. 10 is a partial elevational schematic view of one embodiment for lens arrangement for the present invention.

As seen in FIG. 10, individual lenses 300, one such lens provided for each light source 20 is shown. Such individual lenses 300 may be individual positive lenses held in an appropriate carrier plate (not shown), or a suitably sized lenticular plate can be employed. Similarly, as shown in FIG. 8, individual lenses 302 may be optionally mounted in proximity to each positioned container, shown here as sample tubes 50 in sample tube holder 45. Optical signal level can be enhanced by using individual lenses 300 (FIG. 10), 302 (FIG. 8) or both 300 and 302.

Figure 19:
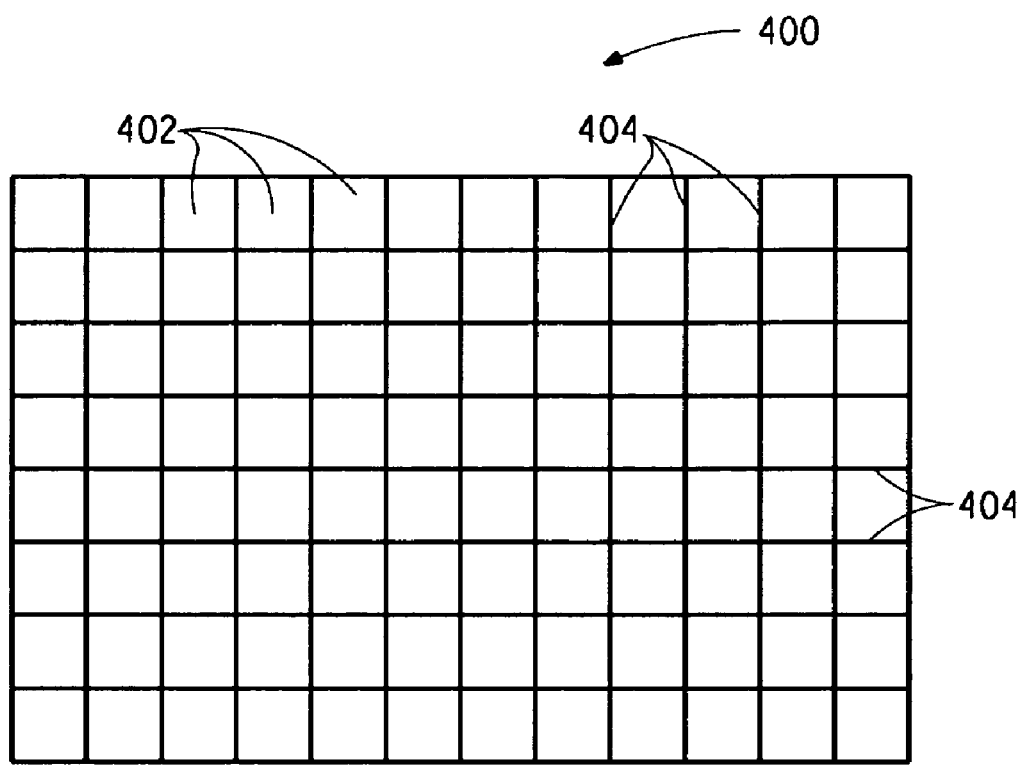
FIG. 19 is a plane view of a "pixelated" fresnel lens useful in the present fluorometer.

The first optical path means can further comprise a pixelized fresnel lens 400 (see FIG. 19) to prevent exciting more than one sample in a container at a time. This type of lens can be described as "pixelized" because such a lens is divided into isolated domains 402, similar to opto-electronic pixels. In this preferred embodiment, the excitation light is prevented from moving laterally and exciting sample in more than one container. This occurs in an unmodified lens due to the finite thickness of the lens permitting scattered rays to bounce off the inside of the two surfaces. Thus, a weakly emitting sample whose output is being sensed can have its signal improperly enhanced by cross talk simultaneously exciting a strongly-emitting sample to yield a false reading.

Referring again to FIG. 19, in the "pixelized" embodiment of the present invention, a fresnel lens can be mounted on a relatively-thin, suitable perforated substrate and the lens can be cut to form grooves 404 that essentially do not penetrate the substrate. Then, grooves 404 can be filled with black paint or other means of blocking light. One method of fabricating a pixelized lens useful in the present invention is to glue a full lens onto a substrate, machine the grooves through the lens to form the sub-lenses and to fill the grooves with black paint or the like. Another technique is to EDM a stainless steel plate to form the barricade grid and to insert the sub-lenses into this grid.

Another mechanism to inhibit lateral transmission of light in a fresnel lens is to employ paper thin fresnel lenses in which the opposing surfaces are so close that laterally transmitted light is dissipated before it reaches an adjacent container. This has been demonstrated by shining laser light by hand onto an 18 mil thick fresnel lens to observe dissipation. An 8 to 15 mil thick pixelized lens is preferred.

The present fluorometer may further optionally comprise an excitation filter in the first optical path means which allows transmission therethrough of an excitation wavelength from the light generated from each light source to its corresponding positioned container, see for example FIG. 2, excitation filter 26.

The excitation filter may be optional if the low heat-generating light sources emit a suitable sufficiently narrow wavelength band, or the excitation band and the emission band are sufficiently separated.

The excitation filter is chosen for a selected wavelength which will excite the selected fluorescing medium used in the sample and generate fluorescent emissions. Thus, it is the light of this selected wavelength that passes through the excitation filter and may be guided via other optics of the first optical path means to the sample to be analyzed. Filters can be expensive components of a fluorometer. It is technically feasible to use filters equal in area to the positioning means, such as a sample holder containing an array of sample tubes. However, filters of such a size could be prohibitive in cost. In the present invention, since the light source can be distributed so as to be equally spaced relative to the positioned containers, the present invention permits reasonable spreading of the light sources while maintaining small filter dimensions. A significant improvement in cost results from this simple expedient. Thus, a small excitation filter can be used relative to the size of the area of light focus, e.g. the containers in the positioning means. For example, an excitation filter with a nominal diameter of about one inch can be used with a preferred conventional sample tube holder size which has an area of about 12 square inches yielding a ratio of excitation filter area to focusing means area of about one-fifteenth.

In order to analyze a variety of samples, it is preferred that the excitation filter be readily replaceable with excitation filters having different pass band characteristics depending upon the particular sample of interest.

The present fluorometer further includes, as shown for example in FIG. 2, means for sensing optical signals 36. The optical signal sensing means is in optical communication with any fluorescing sample in a positioned container and receives and senses photons defining the fluorescent emissions by the particles when excited by the light beam. The fluorescent emissions received by the optical signal sensing means result in a bombardment of the means by photons with each photon resulting in a charge or signal pulse which is counted. The number of sensed photons is counted and the total count from the sample over a fixed period is a measure of the number of fluorescent particles in the sample. Suitable optical signal sensing means include a vacuum photodiode or an avalanche photodiode, a photomultiplier tube (PMT) which generates an output charge or signal pulse in response to each photon sensed by the PMT and a charge coupled device (CCD) type camera, commercially available, which acquires an image of the entire sample tray. When a CCD type camera is used, the light sources can be powered simultaneously. When a PMT is used, the light sources can be powered sequentially. For reasons of sensitivity, a PMT is preferred. The construction of a PMT is well known and PMTs can be temperature controlled. A Hamamatsu PMT Detector Assembly HC-125u available from Hamamatsu USA (360

Foothill Rd. Bridgewater, N.J. 08807) is a suitable representative PMT. The optical signal sensing means is preferably in communication with a programmable control means for measuring fluorescence and analyzing results.

The present fluorometer may further comprise means for calibrating the optical signal sensing means. Suitable calibrating means can be an LED 27 (see FIG. 3) and associated circuitry, which emits the approximate wavelength of an excited, e.g. fluorescing, sample. This calibrating LED can be used to periodically calibrate the optical signal sensing means.

The present invention may further comprise means for measuring the fluorescence by quantifying the amount of fluorescence generated. Such a fluorescence measuring means can simply be a voltmeter in electrical communication with the optical signal sensing means. Alternatively, it can be part of a programmable control means as further discussed below. Such a fluorescence measuring means can be provided by a computer so that a recorded response can be assigned to each selected sample which recorded response can be compared to a pre-determined reference response.

The present fluorometer includes a second optical path means for guiding emitted light from any fluorescing sample to said optical signal sensing means. As with the first optical path means, the second optical path means may include a variety of optics in a variety of arrangements (see FIGS. 2, 3, 4, 5, 7, 11, 13, 14, 15*a*, 15*b*, and 16) and the light so guided can be straight, relatively straight, angled or bent. Optics for the second optical path means can include at least one of the following: a lens, including a condensing lens, an objective lens, a fresnel lens, an imaging lens, a positive lens, or a field lens, a reflector, such as a mirror, a beam splitter, and optionally an emission filter. The emission filter is not necessary if the sensor has a sufficiently narrow selective wavelength detection.

These optics and other useful optics are well known in the art and are commercially available. The second optical path can be at a selected angle to said first optical path. The selected angle can range from 0 to about 25°. For better performance, the angle should be minimized. When the selected angle is zero, a beam splitter can be included in the second optical path of the present fluorometer, see for example dichroic reflector 28, as shown in FIG. 2. The first and second optical path means may share at least one optic.

The second optical path means can include at least one lens optically upstream of the optical signal sensing means. FIGS. 3 and 11 shows such a variant on the second optical path. In FIG. 3, light generated from each sample passes back through field lens 29 and is bent to the incoming light energy and a portion of it falls on emission filter 34. Light passing through emission filter 34 then travels to optical signal sensing means 36. In FIG. 11, field lens 29 is placed between the positioning means, such as sample plate 30 and optical signal sensing means 36. Field lens 29 can be a fresnel lens. Alternatively, a pair of lenses can be used to minimize aberrations.

An advantage of the embodiment of second optical path means shown in FIG. 4 is that an additional optical signal sensing means 36 can be installed symmetrically opposite the one shown in FIG. 4 to increase sensitivity.

It is possible for the second optical path means to be aligned with the first optical path means by providing optical fibers communicating with the apex of the containers which in the combined fluorometer and thermal cycler of the present invention would pass through the heated holder. Light at the apex of containers can be particularly bright. In this embodiment, individual fiber optic lines connect each container to the emission filter and the optical signal sensing means. Optical signal levels are larger than without the use of the fiber optic lines but require the added complication of many optical fibers and for the combined thermal cycler and fluorometer of the present invention, a more complex heated holder. A filter and a field lens may be used in this embodiment.

The present invention includes an emission filter in said second optical path for allowing transmission therethrough of emitted light from any fluorescing sample and for substantially blocking transmission of light of wavelengths other than the wavelengths of said emitted light. As shown in FIG. 2, for example, emission filter 34 is positioned in the second optical path means between containers 32 and optical signal sensing means 36. The emission filter can be in close proximity to the optical signal sensing means or the emission filter can be spaced apart from the optical signal sensing means. Emission filter 34 has a band pass characteristic which removes from the light to be received by optical signal sensing means 36 substantially all light having a wavelength other than the wavelength of fluorescent emission at which the particles fluoresce.

As shown, for example, in FIG. 11, emission filter 34 is preferably spaced apart from optical signal sensing means 36 so that the emitted light is confined to an included conical angle "a" of less than about forty-five degrees. Scattered light will fall outside of the active cone and not be a source of noise.

To eliminate stray light and light reflections which can directly or indirectly adversely affect the detection of fluorescence by the optical signal sensing means, the interior of any housing for the fluorometer is preferably black. Further, the present fluorometer can comprise suitable light traps provided in the form of a well or depression formed in the housing wall to prevent light scattering, secondary fluorescent emissions, etc.

As shown in FIG. 7 for a combined fluorometer and thermal cycler of the present invention, but also applicable to a fluorometer alone, because some light emitted by light sources 20 can pass directly through dichroic mirror 203, dichroic mirror 203 can reflect from the interior of upper unit 204 and impact on optical signal sensing means 36 causing noise. To minimize this effect, light trap 206 can be used. Light trap 206 can be two polished black surfaces angled, for example, at about forty-five degrees, to cause the unwanted light, in large part, to be absorbed harmlessly. As a result, the optical signal sensing means receives substantially only fluorescent emissions caused by the light beam striking the fluorescent particles in the sample to assure that the emission, and in particular the photons of the emissions are the result of fluorescence caused by the light beam only. This significantly enhances the accuracy of detection by the optical signal sensing means.

With the confocal arrangement of FIG. 7, there is found a background to weakest signal ratio of about 15 fold which can be undesirable. As shown in FIG. 13, such noise arises from excitation light scattered in the confocal system to the emission filter 34 at angles greater than about forty-five degrees which emission filter 34 cannot reject. This light passes into optical signal sensing means 36. This noise problem can be resolved by using an arrangement, such as is shown in FIG. 14, where one or more off-axis optical signal sensing means 36 are used with lens 29 in contact with emission filter 34 which is spaced apart from optical signal sensing means 36. Preferably the area between lens 29 and optical signal sensing means 36 is enclosed with a light absorbing material such as black velvet. Front surface mirror 205 can be used to direct light to the containers from the light sources.

Figure 16:
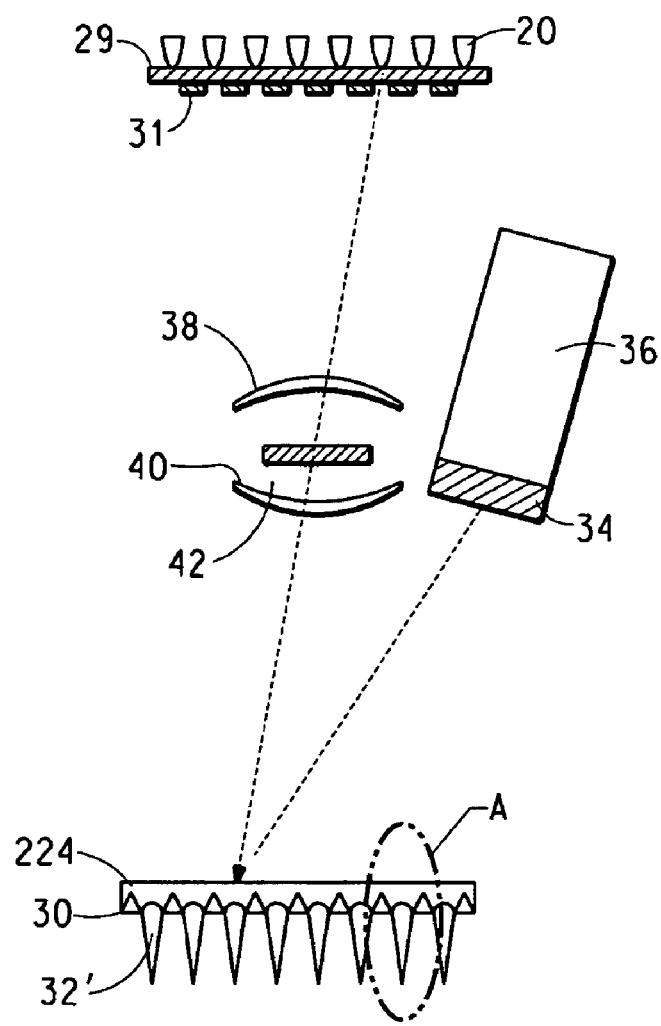
FIG. 16 is a schematic view of another preferred embodiment of the present invention showing the use of different containers and holder.
Figure 17:
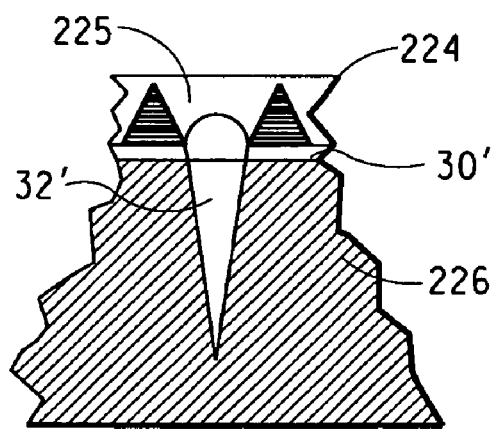
FIG. 17 is an enlarged sectional view of the area denoted "A" in FIG. 16.

FIGS. 16 and 17 show an embodiment of the present invention that can reduce crosstalk that is derived from the filters and particularly cross talk between samples. This preferred embodiment uses a minimum of optical elements in order to reduce scattering and simultaneous excitation of many samples. Such erroneous excitation could indicate a false positive in a container in which amplification has failed lending credence to a false negative result.

Meniscus lenses 38 and 40 are shown, for example, in FIGS. 3, 4, 5, 7, 13, 14, 15a, 15b, 16, and 18a. These type of lenses can be coated to reduce reflections to a minimum. Melles Griot-079 coating, a preferred material, has a reflectance of approximately 0.1% at 485 nm. This can be compared to a MgF coating with approximately 1.0% reflectance which has been found to contribute to 52% of the observed sample cross talk for all positions except one. Such meniscus lenses can be optionally asymmetric relative to the excitation filter in order to avoid scatter to the emission filter which becomes transparent at incident angles greater than 45 degrees while viewing the opposite side of positioning means, such as a sample tray. This must be done in a way that a support structure for the lens does not obscure a direct ray from the excitation filter to any of the samples. The system is non-telecentric both to excitation light and fluorescent light when not using a fresnel lens proximate the containers. This decreases the scatter of excitation light beyond the container being illuminated.

The fluorometer of the present invention may further comprise programmable control means for managing at least one function of the fluorometer. Such functions can include, for example, powering the light sources, sequencing the various operations performed by the fluorometer, receiving data from uniformizing means and comparing such data to reference voltage, measuring the amount of fluorescence emitted from each sample, comparing the amount of fluorescence emitted from each sample with a reference value, further processing resultant information, and other desirable functions known by those of skill in the art. Suitable programmable control means includes computers, such as a microprocessor, personal computer or equivalent, and their associated peripherals and software. Methods of programming computers to perform such functions are well known by those of ordinary skill in the art.

As shown in FIGS. 18b and 9c, programmable control means 500 can be suitably programmed to operate the functions of the fluorometer, and if desired, other instrumentation with which the fluorometer can be combined. Digital outputs acting through light source drive circuitry 502 energize the individual members of the plurality of light sources 504, such as each LED in an array, in a selected pattern. This may be modified by a feed back system with one or more photodiodes 506 to correct for changes in light source output. Response signals generated in the optical signal sensing means 508, which can be, for example, a PMT module or a photodiode, act upon the programmable control means 500 through an A/D input. Where the fluorometer of the present invention is used in combination with a thermal cycler 510, programmable control means 500 may further control the thermal cycler, for example, through a serial output.

The present fluorometer can be operated in the following manner. Upon energizing the light sources, a light beam passes along first optical path means through the excitation filter wherein an excitation wavelength, e.g. 450 nm (blue), passes therethrough and is focused onto the sample in a corresponding positioned container and stimulates the fluorescing particles in the sample to generate fluorescent emissions of a predetermined wavelength, e.g. 520 nm (green). Once light contacts the potentially fluorescing sample in the positioned container only sample that is excited by the light fluoresces in the wavelength range. The fluorescent emission is then guided along the second optical path means to the optical signal sensing means which detects by photon count or image the emitted light. The fluorescence of each sample can then be measured, for example, by comparing the emitted light level to a pre-determined reference level.

The present invention also concerns a combined fluorometer and thermal cycler, comprising the fluorometer described above, wherein the containers are sample tubes, in combination with a thermal cycler, said thermal cycler comprising a thermally controlled base having a plurality of wells, each well capable of holding a capped sample tube in close contact; a thermally controlled cover having a plurality of apertures corresponding to each sample tube, said cover in operative condition mechanically biasing the cap of each said sample tube into said close contact, each said aperture expanding outward from said cap; and programmable control means for controlling the temperature of said sample tubes according to a selected protocol. The thermal cycler can further include elements and systems known to those of skill in the art. Such elements and systems are described, for example, in U.S. Pat. Nos. 5,038,852; 5,333,675; and 5,475,610, all incorporated by reference herein. The said combined fluorometer and thermal cycler of the present invention may further comprise means to collect and process the resultant data to obtain a meaningful result.

Figure 6:
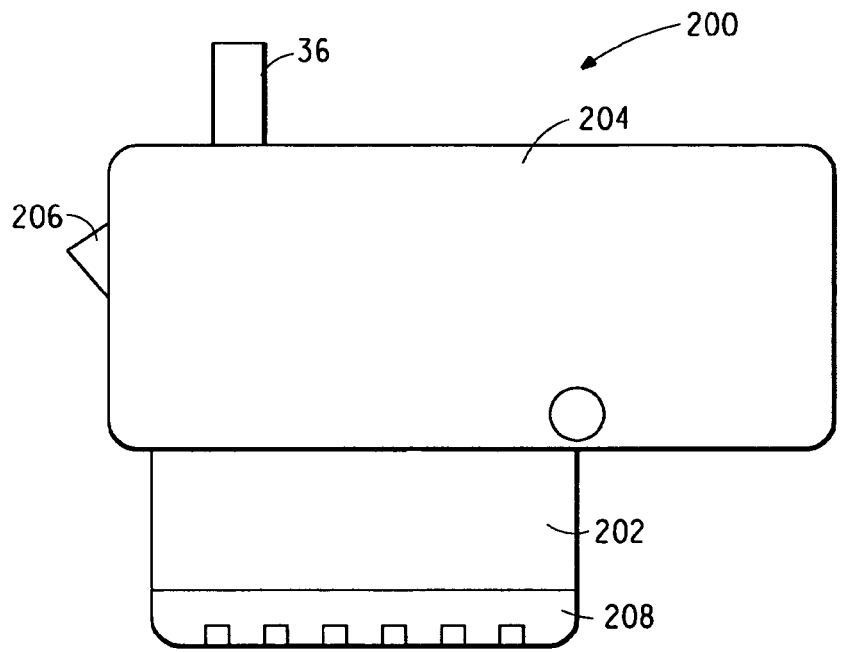
FIG. 6 is a side elevational view of a thermal cycler in combination with a fluorometer of the present invention.

In FIG. 6 there is illustrated one embodiment for a combined fluorometer and thermal cycler of the present invention. In the elevational view shown, the combined fluorometer and thermal cycler 200 has a base unit 202 which has pivotally mounted thereon upper unit 204. Also visible is optical signal sensing means 36. The external side of light trap 206 can be seen. Base unit 202 can be fabricated on thermoelectric heater/cooler 208 which is an operative unit for temperature cycling under control of control means, such as a computer, which is not shown. An Alpha Unit™ Block Assembly for PTC DNA Enginem Systems made by MJ Research, Inc. (590 Lincoln Street, Waltham, Mass. 02451) can be used for the thermoelectric heater/cooler 208.

Referring now to FIG. 7, internal elements of FIG. 6 can be seen. Upper unit 204 and base unit 202 are seen with the covers broken away. In upper unit 204 there is found main frame 210. Similarly, in base unit 202 there is base frame 212. These frames, and thus their respective units, pivot on shaft 214. Shown closed, the arrow indicates the direction which upper unit 204 follows when opened. First sub-frame 216, fastened to main frame 210 by means not shown mounts optical elements, lenses 38 and 40, which are visible, and an excitation filter and stop which is not seen but is mounted midway between the two lenses. Extension frame 218 which is rigidly connected to first sub-frame 216 supports light source support plate 221 which carries an array of light sources 20, such as LEDs, which are aimed toward the center of lens 38. Dichroic mirror 203 is mounted to main frame 210 by means not shown. Second sub-frame 222 is an integral part of main frame 210 but extends into base unit 202. Second sub-frame 222 carries fresnel lens 29 which is disposed in assembly 230 in spaced proximity to thermally controlled cover 224. Thermally controlled cover 224 can be an electrically heated plate that is temperature controlled. Electrical details for such heating and control means are common knowledge.

The present combined fluorometer and thermal cycler includes a thermally controlled base having a plurality of wells, each well capable of holding a capped sample tube in close contact. Shown in FIG. 8 are wells 33 in thermally controlled base 226. These wells can be formed with highly reflective surfaces, both side and bottom, which is preferable when transparent sample tubes are used. This highly reflective characteristic can be accomplished by preparing thermally controlled base 226 from aluminum and polishing the inside of wells 33. Other means can serve this purpose including the use of reflective paint and the like. This configuration concentrates emitted light back into the working elements.

The present combined fluorometer and thermal cycler includes a thermally controlled cover having a plurality of apertures corresponding to each sample tube, said cover in operative condition mechanically biasing the cap of each said sample tube into said close contact, each said aperture expanding outward from said cap. As shown in FIG. 8 in order to provide optical access to sample tubes 50 carried in sample tube holder 45 which is inserted into thermally controlled base 226, thermally controlled cover 224 is provided with suitable spaced apertures 225, one for each sample tube 50. One variant of apertures 225 is illustrated in FIG. 8. Thermally controlled cover 224 applies a downward force to the tops of capped sample tubes 50 to insure adequate heat transfer from suitably shaped wells 33 in thermally controlled base 226 which is heated and cooled by heater/cooler 208 shown in FIG. 7. The downward force to the tops of sample tube caps can be accomplished by slidingly mounting assembly 230 of thermally controlled cover 224 and field lens 29 in sub-frame 222 and providing a biasing means such as springs 228.

Figure 1:
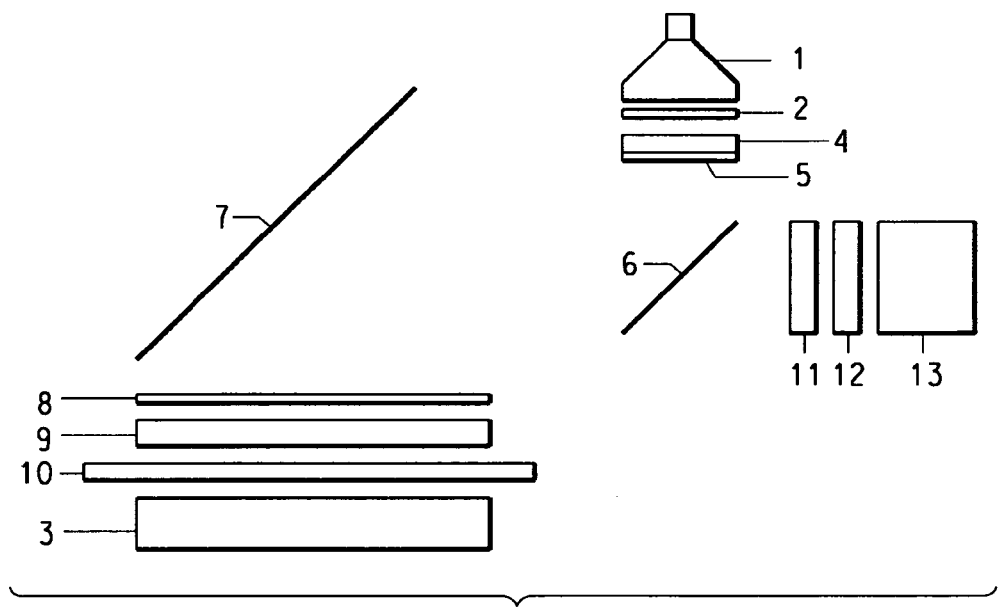
FIG. 1 is a schematic drawing of an optical system of the prior art.
Figure 1A:
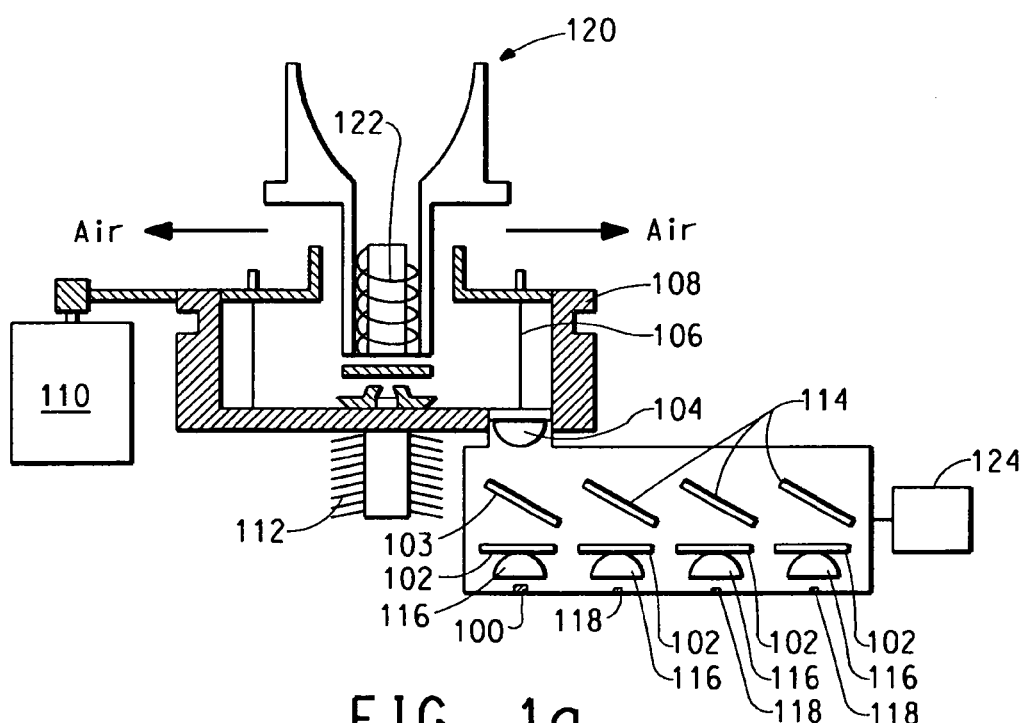
FIG. 1a is a schematic drawing of an optical system of the prior art along with a thermal cycling system.

Apertures 225, shown in FIG. 8, can constitute an included angle of approximately 10 degrees opening outwardly toward the optical signal sensing means. This particular included angle increases light concentration compared to conventional straight sided apertures as in FIG. 1. FIG. 12 shows another embodiment for aperture 225 useful in the present invention. Here the aperture is formed as a parabolic reflector, a configuration which, at the expense of more complicated fabrication, provides even greater light concentration.

It will be noted that sample tube 50 shown in FIGS. 8 and 12 has neck portion 35 extending above sample tube holder 45 into which cap 37 fits. This region between thermally controlled base 226 and thermally controlled cover 224 allows scattered light from one sample tube to impinge on neighboring sample tubes. A significant source of noise can come from cross talk between sample tubes when dealing with weakly emitting samples positioned adjacent to strongly emitting samples. This problem can be addressed by reducing the space between thermally controlled cover 224 and thermally controlled base 226. In order to reduce the space between thermally controlled cover 224 and thermally controlled base 226, positioning means with the containers integrally formed therein can be used. For example, such an embodiment can be found in MJ White Plate 224 ("multiplate" available from MJ Research, Waltham, Mass. 02451). In this multiplate, sample tubes 50 are integrally formed in sample tube holder 45 so that only caps 37 extend above the surface of thermally controlled base 226 and caps 37 then fit into apertures 225 in thermally controlled cover 224.

The "White Plate" is fabricated in a white plastic which is reflective. Polishing of the wells may not be necessary when the white multiplate is used. The white multiplate in a black anodized heater block yields a 5.32 fold increase in signal relative to certain commercially available frosted titer tubes. The same multiplate plate in a shiny cavity yields a 12.9 fold increase over these same frosted titer tubes. By increasing the amount of titanium dioxide in the multiplate plastic material, it is believed that the 12.9 fold increase can be achieved without polishing the cavities in the thermally controlled base.

Figure 15A:
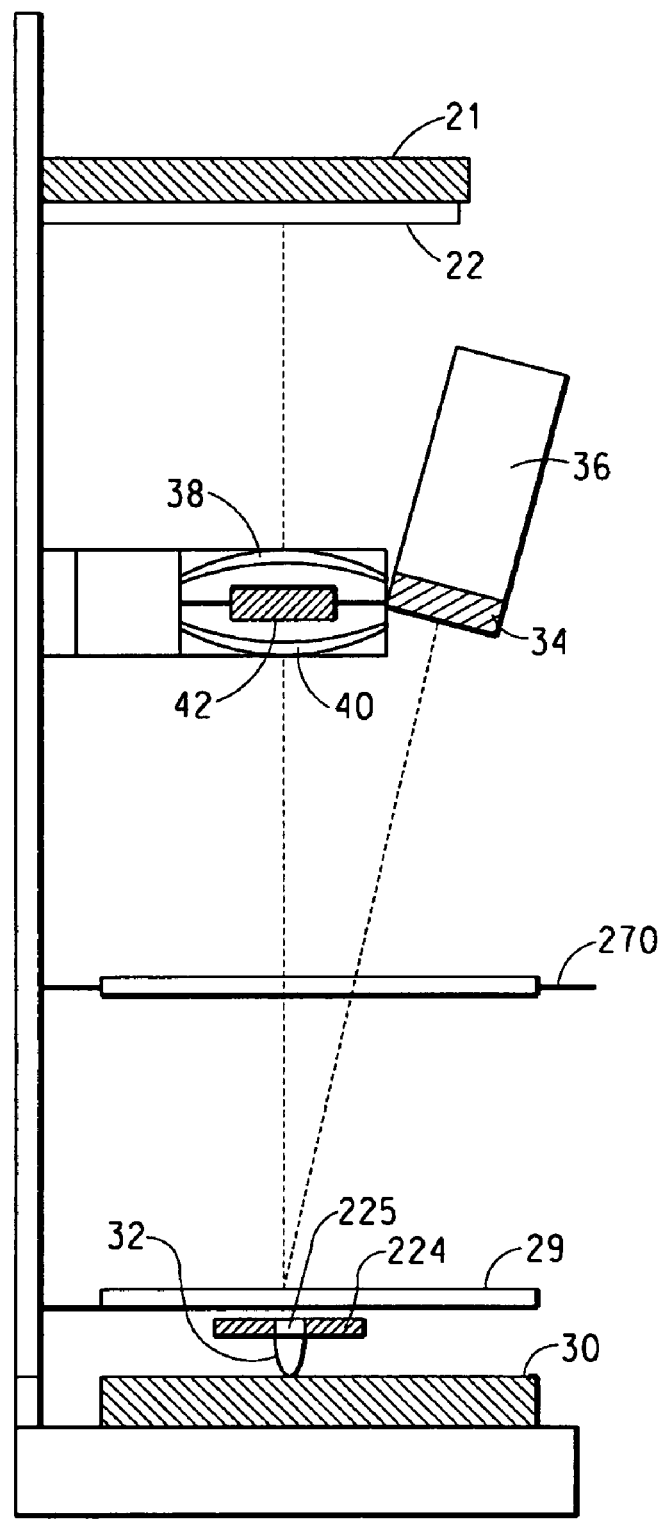
FIGS. 15a and 15b are schematic diagrams of a further embodiment of elements of the present invention.

Another embodiment for reducing or eliminating noise is shown in FIG. 15a. In this embodiment no mirror is present. Field lens 22 can be, for example, about a six inch focal length fresnel lens in contact with the bottom of light source holder 21 in which the light sources can be mounted in parallel. Meniscus lenses 38 and 40, can each be, for example, of about a six inch focal length. There is shown baffle 270 with a black velvet surface facing optical signal sensing means 36. Thermally controlled cover 224 and apertures 225, preferably have an included angle of about sixty degrees. This embodiment has been demonstrated to yield a good signal.

Figure 15B:
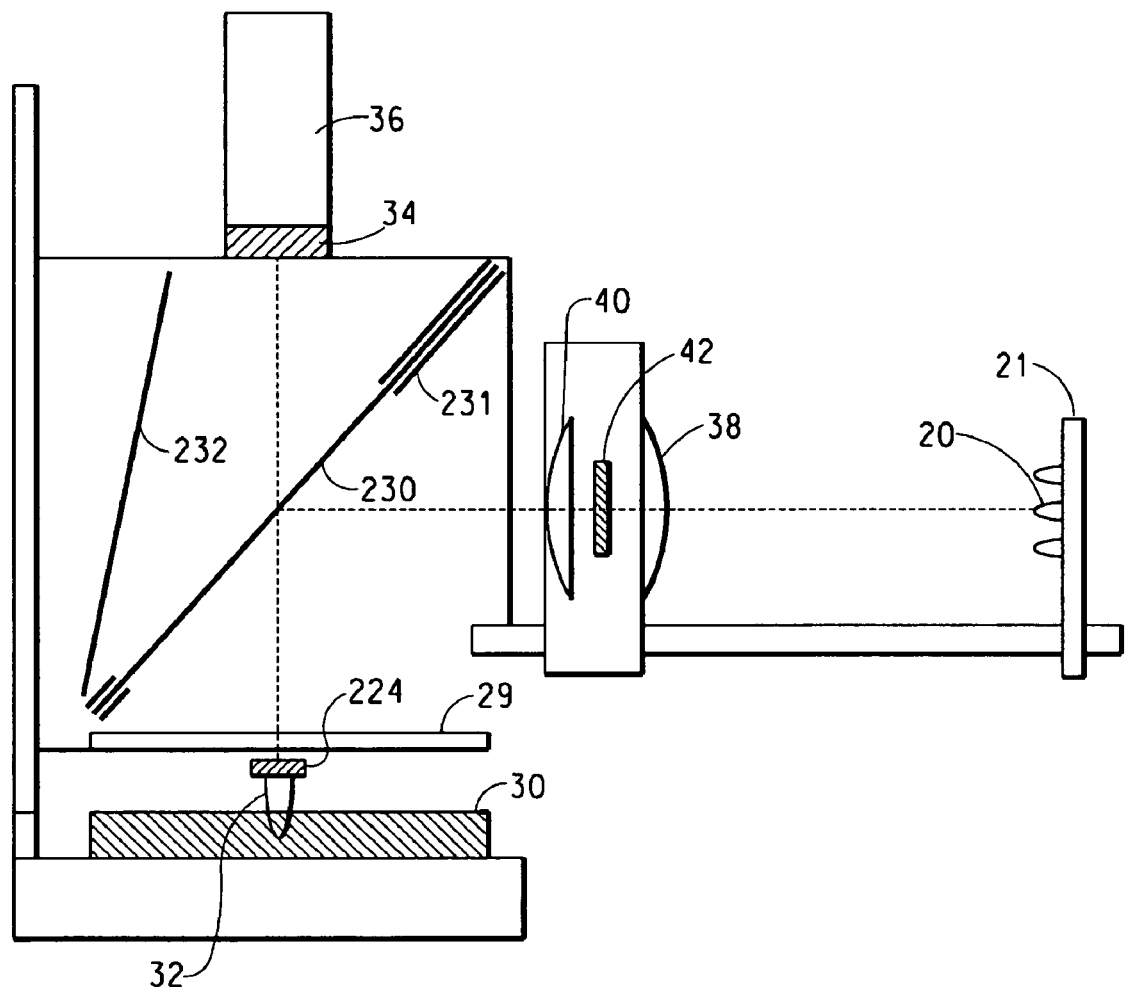

Another embodiment with low measured background noise is shown in FIG. 15b. Mirror 230 is used in this embodiment as a beam splitter. A 40R/60T mirror obtainable from Edmund Scientific (101 East Gloucester Pike, Barrington, N.J. 08007) can be used for mirror 230. Outside of the aperture, the surfaces of mirror 230 are covered with mask 231 which can be, for example, black velvet paper. To further absorb scattered light, the present fluorometer or combined fluorometer and thermal cycler can further comprise a baffle, such as baffle 232, which can be covered with black velvet and placed so as to face optical signal sensing means 36.

The combined fluorometer and thermal cycler of the present invention includes programmable control means for controlling the temperature of said sample tubes according to a selected protocol. Suitable control means for thermal cyclers are known to those of skill in the art. Representative examples of such control means are described in U.S. Pat. Nos. 5,038,852; 5,333,675; and 5,475,610, all incorporated by reference herein. As shown in FIG. 9c, computer 500 can be used to control thermal cycler 510. There can be a different programmable control means for the fluorometer and thermal cycler of the combined fluorometer and thermal cycler of the present invention, or the fluorometer and thermal cycler can be controlled by the same programmable control means.

In use, as shown for example in FIG. 7, a combined fluorometer and thermal cycler 200, is opened by tilting upper unit 204 away from lower unit 202. A tray of sample tubes 50 is inserted in thermally controlled base 226 and combined fluorometer and thermal cycler 200 is closed. Closing of combined fluorometer and thermal cycler 200 forces thermally controlled cover 224 against the tops of the caps of sample tubes 50 ensuring their seating in thermally controlled base 226 and good heat transfer from heater/cooler 208.

After the instrument is closed, polymerase chain reaction (PCR) can proceed. PCR involves a procedure in which separate, complementary-strands of nucleic acid are treated with a molar excess of two oligonucleotide primers (see U.S. Pat. No. 4,683,202 (Mullis)). The primers are extended to form complementary primer extension-products which act as templates for synthesizing the desired nucleic acid sequence. The steps of the reaction, a sequence of thermal treatments, are carried out and are repeated as often as desired. The analyte is cycled between the higher temperature level at which double stranded chains break into single strands and the lower level at which they anneal back to double strands. Typically as many as thirty-five or more cycles are necessary to obtain a number of replicas adequate for further processing. The assay rapidly amplifies desired ("target") strands to a level at which their presence can be indicated. Fluorescent dyes are preferred as indicators, particularly intercalating dyes that fluoresce when bound to double stranded DNA but do not bind to single strands and have no or little signal in the presence of single strands. An intercalating dye can be used as an indicator in the sample. A preferred intercalating dye useful as the fluorescing medium is SYBR Green available from Molecular Probes which is sensitive to the excitation wavelength of blue (485 nm). Other fluorescing materials can be used in the sample.

Once the sample is amplified means for powering the light sources can be activated in a desired sequence including simultaneously, preferably by programmable control means, and any optical signal emitted is detected by optical signal sensing means 36. The signal sensed can be used to measure the emitted fluorescence, for example, by comparing the emitted light level to a pre-determined reference which can be through use of an appropriate computer program.

Figure 21:
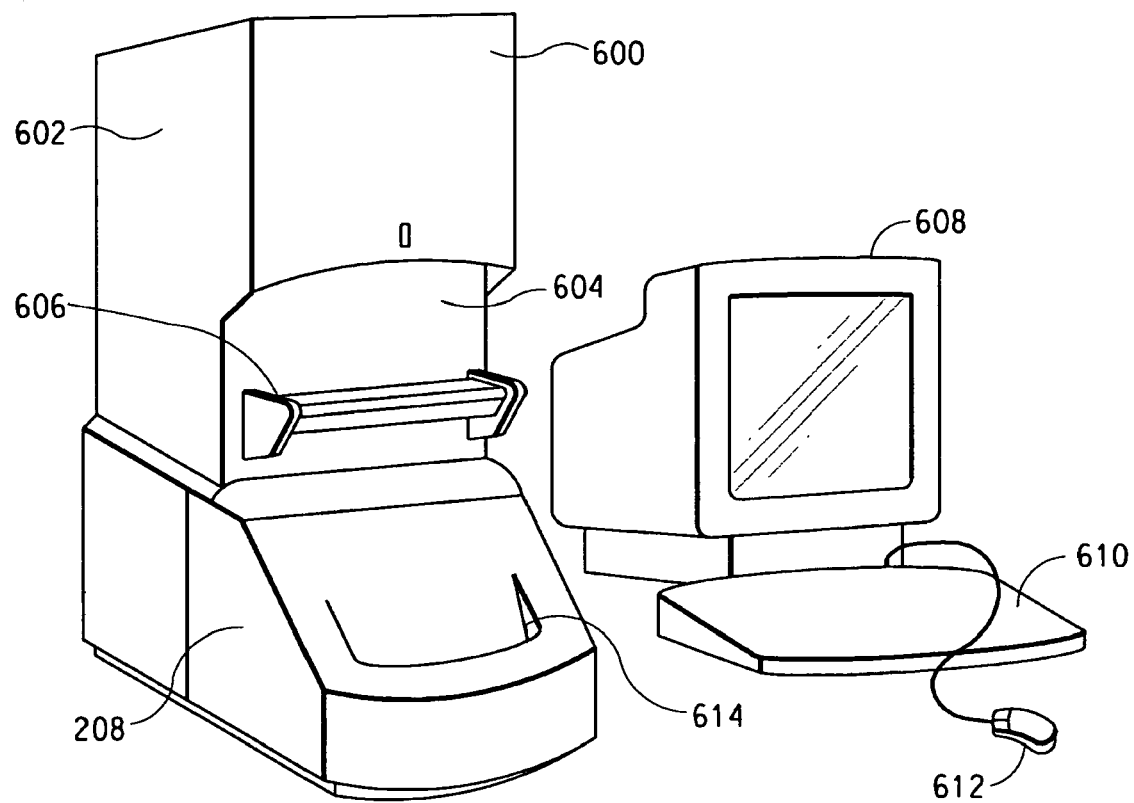
FIG. 21 is a perspective view of a preferred embodiment of the combined thermal cycler and fluorometer of the invention shown with associated desktop computer.

Refer now to FIG. 21. A preferred embodiment of a combined fluorometer and thermal cycler 600 is illustrated. The fluorometer 602 is mounted vertically above a thermal cycler 208. The aforementioned Alpha Unit™ Block Assembly for PTC DNA Engine™ Systems is preferred for this thermoelectric heater/cooler. Also shown are the means for control and analysis, PC 608 with keyboard 610 and mouse 612.

This embodiment is based on the off-axis configuration of FIG. 4 with the optical sensing means 36 to the rear of the instrument. A thermally controlled cover such as 224 in FIG. 7 is moved up and down with sliding panel 604 which performs several functions as will be seen. This cover 224 is spring-biased as by springs 228 of FIG. 7. Access to fluorometer 602 for input and removal of sample trays is initiated by raising vertical sliding panel 604 using handle 606. This motion raises locking pins, not shown, that hold cycler 208 in optical alignment with light sources 20 (see FIG. 4) and permits the operator to pull cycler 208 forward from beneath fluorometer 602 for loading/unloading exactly as in its use as a stand-alone thermal cycler. Handle 614 facilitates this pulling and pushing the cycler into and out of its operating position.

The present invention can be employed in several end uses. For example, the present combined fluorometer and thermal cycler can be used for melting curve analysis. In this application, sample tubes containing solutions of sample material, such as DNA or RNA, in sufficient amount and with a suitable indicator such as an intercalating dye that fluoresces mainly when bound to double stranded molecular chains, can be placed in a thermally controlled base of a combined fluorometer and thermal cycler of the present invention and a temperature ramp can be actuated. Melting curve can then be performed and meaningful results obtained indicating the presence of particular molecular chains. Preferred melting curve analysis is done via the method disclosed in Provisional Application No. 60/131,901, commonly owned with the present application, the contents of which are incorporated herein by reference. Establishing the presence of dangerous pathogens is one preferred end use.

When an instrument of the present invention is to be employed in melting curve analysis, as set forth in the provisional application mentioned above, it is not necessary to provide the same expensive temperature control apparatus as is normal to a thermal cycler. In a thermal cycler, the temperature must be changed accurately in seconds from an elevated temperature (ordinarily about 70° Celsius) to a higher level (about 90° Celsius) and reversed by cooling for about 35 cycles. In this melting curve analysis, the temperature must be ramped accurately over a period of about an hour between the same temperatures but the cooling is not critical. Hence such apparatus might well be termed a "ramper" and can be combined with the fluorometer of the present invention.

The present combined fluorometer and thermal cycler can be used to perform PCR to amplify a small amount of genetic matter to a readable level and thereafter determine the presence or absence of known sequences of nucleic acids or the presence or absence of known organisms by fluorometry. Thus, the present invention provides a method for analyzing polymerase chain reaction amplified material, comprising the steps of positioning the material into optical communication with the light sources of the fluorometer or the combined fluorometer and thermal cycler described above; exposing the material to an excitation wavelength; detecting the emitted light with the optical signal sensing means; and comparing the emitted light level to a pre-determined reference level. These steps are as described above. Comparing the emitted light level to a pre-determined reference level can be done with programmable means, such as a computer with the appropriate software. Such programmable means and software are known to those of skill in the art and can be the same as or separate from the programmable means that can be used with the fluorometer or can be used with the combined fluorometer and thermal cycler of the present invention. In the present method, the amplification of the sample material can be by exposure to a selected DNA annealing/denaturing temperature range which comprises multiple cycles.

Analysis of the PCR amplified material in the present method comprises detection of the fluorescence signal and can further include DNA melting curve analysis. Thus, the present method can further comprise collecting melting curve data and identifying an unknown DNA according to algorithms predictive of an examined DNA sequence relative to teachings by known DNA sequences. In this particular embodiment, the amplification of the sample material can be by exposure to a selected DNA annealing/denaturing temperature range which comprises a single cycle.

What is claimed is:

1. A fluorometer comprising:
a plurality of light sources, wherein each of said light sources generates heat at a level below which active cooling is required;
a plurality of containers for containing a potentially fluorescing sample;
a first optical path means;
a second optical path means; and
a means for sensing optical signals,
wherein there is an equal number of said light sources and said containers, each of said containers corresponds to one of said light sources, and said fluorometer does not comprise a positioning mechanism for repeatedly presenting said containers to said light sources during operation of said fluorometer; and
wherein said first optical path means is located between said plurality of light sources and said plurality of containers, said first optical path means is straight or relatively straight, said first optical path means does not comprise a fiber optic line, said second optical path means is located between said plurality of containers and said means for sensing optical signals, and said means for sensing optical signals is in optical communication with said containers.

2. The fluorometer of claim 1, wherein said first optical path means comprises a lens.

3. The fluorometer of claim 1, wherein said second optical path means comprises a lens.

4. The fluorometer of claim 1, wherein said first optical path means comprises a lens and said second optical path means comprises a lens.

5. The fluorometer of claim 1, wherein said first optical path means comprises a plurality of lenses, wherein each of said plurality of lenses corresponds to one of each of said light sources.

6. The fluorometer of claim 1, wherein said second optical path means comprises a plurality of lenses, wherein each of said plurality of lenses corresponds to one of each of said containers.

7. The fluorometer of claim 1, wherein said first optical path means comprises a first plurality of lenses and said second optical path means comprises a second plurality of lenses, wherein each of said first plurality of lenses corresponds to one of each of said light sources and each of said second plurality of lenses corresponds to one of each of said containers.

8. The fluorometer of claim 1, wherein said first optical path means is located in proximity to said light sources relative to said second optical path means and said plurality of containers, and said second optical path means is located in proximity to said containers relative to said first optical path means and said plurality of light sources.

9. The fluorometer of claim 1, wherein said light sources are light emitting diodes.

10. The fluorometer of claim 9, wherein said light emitting diodes are blue.

11. The fluorometer of claim 1, further comprising a programmable controller for controlling at least one function of the fluorometer.

12. The fluorometer of claim 1, wherein said containers comprise sample tubes.

13. The fluorometer of claim 12, wherein said sample tubes are held in position by a sample tube holder or a multiplate.

14. The fluorometer of claim 13, wherein said sample tubes form an array, and said light sources, first optical path means, and second optical path means are arranged in corresponding arrays.

15. The fluorometer of claim 14, wherein said array is an 8 by 12 sample array.

16. The fluorometer of claim 1, wherein said means for sensing optical signals is selected from the group consisting of a photomultiplier tube, a charge coupled device type camera, a vacuum photodiode, and an avalanche photodiode.

17. The fluorometer of claim 1, further comprising at least one reflector positioned to guide light emitted by a fluorescing sample from at least one container to said means for sensing optical signals.

18. The fluorometer of claim 1, wherein at least one of said plurality of containers contains a potentially fluorescing sample.

19. A method for analyzing a sample, comprising the steps of:
(a) providing a sample in at least one of the plurality of containers in the fluorometer of claim 1;
(b) generating light from at least one of the plurality of low heat generating light sources;
(c) guiding the generated light from said at least one light source through its corresponding first optical path means to its said corresponding container in which said sample is provided; and
(d) detecting for a fluorescing signal from said sample with said means for sensing optical signals.

20. An apparatus comprising:
(a) the fluorometer of claim 1; and
(b) a thermal cycler.

* * * * *